United States Patent
Kuechler et al.

(10) Patent No.: US 7,084,319 B2
(45) Date of Patent: Aug. 1, 2006

(54) CATALYST FLUIDIZATION IN OXYGENATE TO OLEFIN REACTION SYSTEMS

(75) Inventors: Keith Holroyd Kuechler, Friendswood, TX (US); Nicolas P. Coute, Houston, TX (US); Jeffrey Scott Smith, Seabrook, TX (US); Stephen Harold Brown, Brussels (BE); Richard B. Hall, Whitehouse Station, NJ (US); Teng Xu, Houston, TX (US); Stephen Nell Vaughn, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 438 days.

(21) Appl. No.: 10/729,568

(22) Filed: Dec. 5, 2003

(65) Prior Publication Data

US 2005/0124838 A1  Jun. 9, 2005

(51) Int. Cl.
*C07C 1/00* (2006.01)

(52) U.S. Cl. .................................. 585/639; 585/640

(58) Field of Classification Search ......... 585/638–640
See application file for complete search history.

(56) References Cited

U.S. PATENT DOCUMENTS

| | | | |
|---|---|---|---|
| 4,499,327 A | 2/1985 | Kaiser | 585/640 |
| 4,597,771 A | 7/1986 | Cheng | 48/77 |
| 4,670,993 A | 6/1987 | Dunaway et al. | 34/10 |
| 4,677,242 A | 6/1987 | Kaiser | 585/638 |
| 4,677,243 A | 6/1987 | Kaiser | 585/638 |
| 4,684,375 A | 8/1987 | Morin et al. | 48/197 |
| 4,752,651 A | 6/1988 | Kaiser | 585/640 |
| 4,973,792 A | 11/1990 | Lewis et al. | 585/638 |
| 5,475,182 A | 12/1995 | Janssen | 585/640 |
| 5,714,662 A | 2/1998 | Vora et al. | 585/640 |
| 5,744,680 A | 4/1998 | Mulvaney, III et al. | 585/640 |
| 5,817,906 A | 10/1998 | Marker et al. | 585/640 |
| 5,914,433 A | 6/1999 | Marker | 585/313 |
| 5,962,762 A | 10/1999 | Sun et al. | 585/640 |
| 5,990,369 A | 11/1999 | Barger et al. | 585/640 |
| 6,005,150 A | 12/1999 | Vora | 585/324 |
| 6,023,005 A | 2/2000 | Lattner et al. | 585/639 |
| 6,040,264 A | 3/2000 | Sun et al. | 502/214 |
| 6,121,503 A | 9/2000 | Janssen et al. | 585/640 |
| 6,121,504 A | 9/2000 | Kuechler et al. | 585/640 |
| 6,166,282 A | 12/2000 | Miller | 585/638 |
| 6,187,983 B1 | 2/2001 | Sun | 585/638 |
| 6,303,839 B1 | 10/2001 | Marker | 585/313 |
| 6,303,841 B1 | 10/2001 | Senetar et al. | 585/639 |

(Continued)

FOREIGN PATENT DOCUMENTS

GB    2 171 718    9/1986

(Continued)

*Primary Examiner*—Walter D. Griffin
*Assistant Examiner*—In Suk Bullock

(57) ABSTRACT

The present invention provides various processes for fluidizing molecular sieve catalyst compositions in a fluidized bed reaction system. The invention comprises fluidizing a molecular sieve catalyst composition with a reactive fluidizing medium under conditions effective to convert at least a portion of the fluidizing medium to additional product. The invention is ideally suited for implementation into an oxygenate to olefin reaction system, in which the fluidizing medium optionally comprises byproducts of the oxygenate to olefin conversion reaction.

81 Claims, 3 Drawing Sheets

U.S. PATENT DOCUMENTS

| | | | |
|---|---|---|---|
| 6,441,261 B1 | 8/2002 | Kuechler et al. | 585/639 |
| 6,455,747 B1 | 9/2002 | Lattner et al. | 585/638 |
| 6,455,749 B1 | 9/2002 | Vaughn | 585/640 |
| 6,482,998 B1 | 11/2002 | Kuechler et al. | 585/638 |
| 6,482,999 B1 | 11/2002 | Fung et al. | 585/640 |
| 2001/0020116 A1 | 9/2001 | Janssen et al. | 585/638 |
| 2002/0087041 A1 | 7/2002 | Kuechler et al. | 585/638 |
| 2003/0004384 A1 | 1/2003 | Coute et al. | 585/639 |

FOREIGN PATENT DOCUMENTS

| | | |
|---|---|---|
| WO | 97/36845 | 10/1997 |
| WO | 98/02471 | 1/1998 |
| WO | 00/41986 | 7/2000 |
| WO | 01/62689 | 8/2001 |
| WO | 02/32837 | 4/2002 |

CATALYST FLUIDIZATION IN OXYGENATE TO OLEFIN REACTION SYSTEMS

FIELD OF THE INVENTION

The present invention relates to catalyst fluidization. More particularly, the present invention relates to the fluidization of molecular sieve catalyst compositions in an oxygenate to olefin reaction system.

BACKGROUND OF THE INVENTION

Light olefins, defined herein as ethylene and propylene, serve as feeds for the production of numerous chemicals. Olefins traditionally are produced by petroleum cracking. Because of the limited supply and/or the high cost of petroleum sources, the cost of producing olefins from petroleum sources has increased steadily.

Oxygenates such as alcohols, particularly methanol, dimethyl ether, and ethanol, are alternative feedstocks for the production of light olefins. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production. Such conversion processes are referred to as oxygenate to olefin (OTO) conversion processes and occur in OTO reaction systems. In an OTO reaction system, an oxygenate in an oxygenate-containing feedstock contacts a molecular sieve catalyst composition under conditions effective to convert at least a portion of the oxygenate to light olefins, which are yielded from the reaction system in a reaction effluent.

One type of reaction unit useful for conducting an OTO conversion process is a fluidized bed reactor, wherein solid catalyst particles contact a fluidizing medium, which causes the solid catalyst particles to become suspended in a fluidized state during contact with the feedstock and other vapor materials. Steam and/or inert gases typically serve as fluidizing mediums.

Typically, undesirable by-products are formed in OTO reaction systems in addition to the desired light olefins. One method for reducing the production of undesirable by-products in a fluidized bed reactor involves operating in a hydrodynamic flow regime such that the superficial gas velocity obtains a velocity high enough to cause a net flow of catalyst in the reactor in the same direction as the flow of the feedstock and other vapors. That is, the feedstock and other vapors essentially carry the catalyst particles along with them. These flow regimes are known to those skilled in the art as fast-fluidized bed and riser regimes, and are preferred in reaction systems in which a more plug flow reactor type is desired.

Preferred OTO catalyst compositions, which exhibit desirable fluidization and conversion characteristics, include metalloaluminophosphate molecular sieves, e.g., silicoaluminophosphate (SAPO) molecular sieves. Activated metalloaluminophosphate molecular sieves have been found to be sensitive to moisture. In general, significant exposure of the activated molecular sieves to moisture has been found to deactivate the catalytic activity of the molecular sieves. Thus, fluidizing such catalyst compositions with steam as the fluidizing medium may decrease catalyst composition lifetime. As a result, the need exists for fluidizing catalyst compositions that include metalloaluminophosphate molecular sieves without deactivating the molecular sieves contained therein.

In addition, a portion of the undesirable by-products formed in OTO reaction systems includes C4+ olefins. These materials are, in general, less valuable than the desired light olefins, and in some circumstances they may be difficult materials for which to find a market at all. Thus, there is also a need for improved methods to manage these C4+ materials.

There have been disclosed a limited number of methods directed to this area. U.S. Pat. No. 5,744,680 to Mulvaney, et. al., discusses recycling methane recovered from an OTO product as a diluent to reduce water in the reaction zone which was found to adversely affect the activity of the catalyst. U.S. Pat. No. 5,817,906 to Marker, et. al., talks about transforming an OTO feed alcohol to an ether and introducing the ether to the OTO reaction zone to reduce the amount of water contacted with a metal alumino-silicate catalyst to provide extended catalyst life. U.S. Pat. Nos. 5,914,433 and 6,303,839 to Marker assert that cracking C3+ olefins from an OTO reaction in a separate cracking zone over regenerated OTO aluminophosphate catalyst and passing the cracked product to the OTO reactor provides extended catalyst life in the oxygenate conversion zone.

U.S. Pat. No. 6,455,749 to Vaughn touches on the recycle of a heavy hydrocarbon fraction from an OTO reaction to an OTO reactor or separate reactor to convert at least a portion of the heavy hydrocarbons to light olefins. In that reference, it is disclosed that the conversion of C4+ olefins, in particular butene-1, is significantly lower than a typical oxygenate feedstock, in particular methanol, at the same reaction conditions over a silicoaluminophosphate catalyst:

In response to the aforementioned needs, and distinct from the noted references, the present invention simultaneously provides for increased life in the OTO reaction zone through reduced moisture content and improved utilization of C4+ olefins produced by the OTO reaction.

SUMMARY OF THE INVENTION

The present invention provides a practical use for oxygenates and/or heavy olefin by-products, hereinafter alone or together termed "byproducts," contained in an oxygenate to olefin (OTO) reaction system product effluent. In a preferred embodiment, the oxygenate and heavy olefins from the OTO reaction system are separated from the light olefins contained therein, and are utilized as a fluidizing medium in the reaction system. Ideally, the oxygenate and heavy olefins that are used as the fluidizing medium are converted in the fluidization zone of the reaction system to additional light olefins. In this manner, the amount of light olefins produced in the OTO reaction system can be increased. Additionally or alternatively, the fluidizing medium may comprise one or more components that are not by-products of an OTO reaction process.

Specifically, one embodiment of the present invention is directed to a process for producing light olefins. In the process, an oxygenate contacts a molecular sieve catalyst composition in a fluidized reactor under first conditions effective to convert the oxygenate to the light olefins. The molecular sieve catalyst composition and the light olefins are directed to a disengaging zone, from which the light olefins are yielded. The molecular sieve catalyst composition is directed from the disengaging zone to a standpipe. The molecular sieve catalyst composition is fluidized in the standpipe with a fluidizing medium, which preferably is selected from one or more of methanol, dimethyl ether, C4+ olefins, C4+ hydrocarbons, acetaldehyde, acetone, butanone, acetic acid, one or more byproducts formed in the oxygenate contacting step, or a mixture thereof. The fluidizing medium optionally further comprises steam. The molecular sieve catalyst composition is transported in a fluidized manner from the standpipe back to the fluidized reactor. Optionally, the process further includes the steps of separating the one or more byproducts from the light olefins, and directing the one or more byproducts to the standpipe.

The fluidizing step optionally creates a superficial gas velocity (SGV) in an upward direction, and the molecular sieve catalyst composition is transported in a downward direction while in the standpipe. Preferably, the SGV is from about 0.1 to about 1.0 meters/second, more preferably from about 0.2 to about 0.8 meters/second. Alternatively, the SGV is in a downward direction, co-directional with the flow of catalyst. In one embodiment, the fluidizing medium contacts the molecular sieve catalyst composition in one or both the fluidizing step and/or the transporting step under second conditions effective to convert at least a portion of the fluidizing medium to additional light olefins. The first conditions optionally comprise a temperature of from about 204° C. to about 371° C. and an SGV of from about 0.11 to about 15 m/s. The second conditions optionally comprise a temperature of from about 350° C. to about 1000° C. and a superficial gas velocity in an upward direction of from about 0.1 to about 1.0 m/s, and more preferably comprise a temperature of from about 400° C. to about 800° C. and a superficial gas velocity in an upward direction of from about 0.2 to about 0.8 m/s. More specifically, the second conditions optionally comprise a temperature of from about 662° F. (350° C.) to about 1832° F. (1000° C.), preferably from about 752° F. (400° C.) to about 1472° F. (800° C.), more preferably from about 842° F. (450° C.) to about 1382° F. (750° C.), and yet more preferably from about 896° F. (480° C.) to about 1202° F. (650° C.).

The conversion of the at least a portion of the fluidizing medium to additional light olefins optionally occurs at a WHSV of less than 5 $hr^{-1}$, preferably less than 3 $hr^{-1}$. The conversion of the at least a portion of the fluidizing medium to additional light olefins optionally occurs at a weight percent conversion of at least 10 percent, preferably at least about 30 percent. In one embodiment, the process further comprises the steps of directing a first portion of the molecular sieve catalyst composition to a catalyst regenerator; heating the first portion in the presence of oxygen under third conditions effective to at least partially regenerate the first portion and form regenerated catalyst; and directing the regenerated catalyst to one or more of the disengaging zone, the standpipe, or to a standpipe entry zone. The regenerated catalyst optionally contacts the fluidizing medium under conditions effective to increase the selectivity of the regenerated catalyst to light olefins.

In another embodiment, the invention is to a process for fluidizing molecular sieve catalyst composition with a fluidizing medium in a conduit. In this embodiment, the invention includes a step of providing a reaction system comprising a fluidized reactor and a disengaging zone, and further comprising one or more of a stripping unit, a catalyst regenerator, a catalyst cooler, a standpipe, a standpipe entry zone, and a plurality of conduits for transporting a molecular sieve catalyst composition between these units. An oxygenate contacts the molecular sieve catalyst composition in the fluidized reactor under first conditions effective to convert the oxygenate to light olefins. The molecular sieve catalyst composition and the light olefins are directed to a disengaging zone, from which the light olefins are yielded. The molecular sieve catalyst composition is directed from the disengaging zone to a standpipe and from the standpipe to the fluidized reactor. In this embodiment, the molecular sieve catalyst composition contacts a fluidizing medium in one or more of the plurality of conduits under second conditions effective to transport the molecular sieve catalyst composition in a fluidized manner through the one or more of the plurality of conduits. The fluidizing medium preferably is selected from one or more of methanol, dimethyl ether, C4+ olefins, C4+ hydrocarbons, acetaldehyde, acetone, butanone, acetic acid, one or more byproducts formed in the oxygenate contacting step, or a mixture thereof.

In this embodiment, the process optionally comprises the steps of separating the byproducts from the light olefins, and directing the byproducts to the one or more of the plurality of conduits. The one or more of the plurality of conduits optionally comprise a conduit in fluid communication between the disengaging zone and one or more of the stripping unit or the fluidized reactor. Additionally or alternatively, the one or more of the plurality of conduits comprise a conduit in fluid communication between the catalyst regenerator and one or more of the disengaging zone, the catalyst cooler, the standpipe entry zone, the standpipe or the fluidized reactor. Additionally or alternatively, the one or more of the plurality of conduits comprise a conduit in fluid communication between the catalyst cooler and one or more of the disengaging zone, the standpipe, the standpipe entry zone, or the fluidized reactor. Optionally, a superficial gas velocity of from about 0.1 to about 1.0 m/s, preferably from about 0.2 to about 0.8 m/s, is formed in the one or more of the plurality of conduits. The second conditions optionally are effective to convert at least a portion of the fluidizing medium to additional light olefins. The process optionally further comprises the steps of directing a first portion of the molecular sieve catalyst composition to the catalyst regenerator, heating the first portion in the presence of oxygen under third conditions effective to at least partially regenerate the first portion and form regenerated catalyst; and directing the regenerated catalyst to one or more of the standpipe, the disengaging zone, the standpipe entry zone or to the one or more of the plurality of conduits.

In another embodiment, the invention is to a process for increasing the selectivity of a catalyst for light olefins. In this embodiment, the invention includes a step of contacting an oxygenate with a first molecular sieve catalyst composition in a fluidized reactor under first conditions effective to convert the oxygenate to light olefins. The first molecular sieve catalyst composition and the light olefins are directed to a disengaging zone, from which the light olefins are yielded. The first molecular sieve catalyst composition is directed from the disengaging zone to a standpipe. A second molecular sieve catalyst composition, which optionally comprises regenerated and/or fresh catalyst, is directed to one or more of the standpipe, the disengaging zone or an optional standpipe entry zone. The second molecular sieve catalyst composition contacts a fluidizing medium under second conditions effective to increase the selectivity of the second molecular sieve catalyst composition for light olefins. The first and second molecular sieve catalyst compositions are directed in a fluidized manner from the standpipe back to the fluidized reactor. The fluidizing medium optionally contacts the first and/or the second molecular sieve catalyst compositions under third conditions effective to convert at least a portion of the fluidizing medium to additional light olefins. Either or both the first and/or the second molecular sieve catalyst compositions comprise a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, intergrown forms thereof, and mixtures thereof. In this embodiment, the first molecular sieve catalyst composition may become at least partially deactivated in the initial oxygenate contacting step to form a coked catalyst. If so, the process optionally further comprises the steps of directing the coked catalyst from the disengaging zone to a catalyst regenerator, and heating the coked catalyst in the presence of oxygen under third conditions effective to at least partially regenerate the coked catalyst and form the second molecular sieve catalyst composition.

In another embodiment, the invention is to a process for producing light olefins, wherein a molecular sieve catalyst composition is fluidized in a standpipe entry zone. In this embodiment, an oxygenate contacts a molecular sieve catalyst composition in a fluidized reactor under first conditions effective to convert the oxygenate to the light olefins. The molecular sieve catalyst composition and the light olefins are directed to a disengaging zone, from which the light olefins are yielded. The molecular sieve catalyst composition is directed from the disengaging zone to a standpipe entry zone, in which the molecular sieve catalyst composition is fluidized with a fluidizing medium. The fluidizing medium preferably is selected from one or more of methanol, dimethyl ether, C4+ olefins, C4+ hydrocarbons, acetaldehyde, acetone, butanone, acetic acid, byproducts formed in step (a) or a mixture thereof. The molecular sieve catalyst composition is directed from the standpipe entry zone to a standpipe. The molecular sieve catalyst composition is then transporting from the standpipe to the fluidized reactor. The process optionally further comprises the steps of separating the byproducts from the light olefins, and directing the byproducts to the standpipe entry zone. The fluidizing medium optionally contacts the molecular sieve catalyst composition in one or more of the directing, fluidizing and/or transporting steps under second conditions effective to convert at least a portion of the fluidizing medium to additional light olefins.

BRIEF DESCRIPTION OF THE DRAWINGS

Various embodiments of the overall invention are shown by way of example in the attached figures, wherein.

DETAILED DESCRIPTION OF THE INVENTION

A. Introduction

Figure 1:
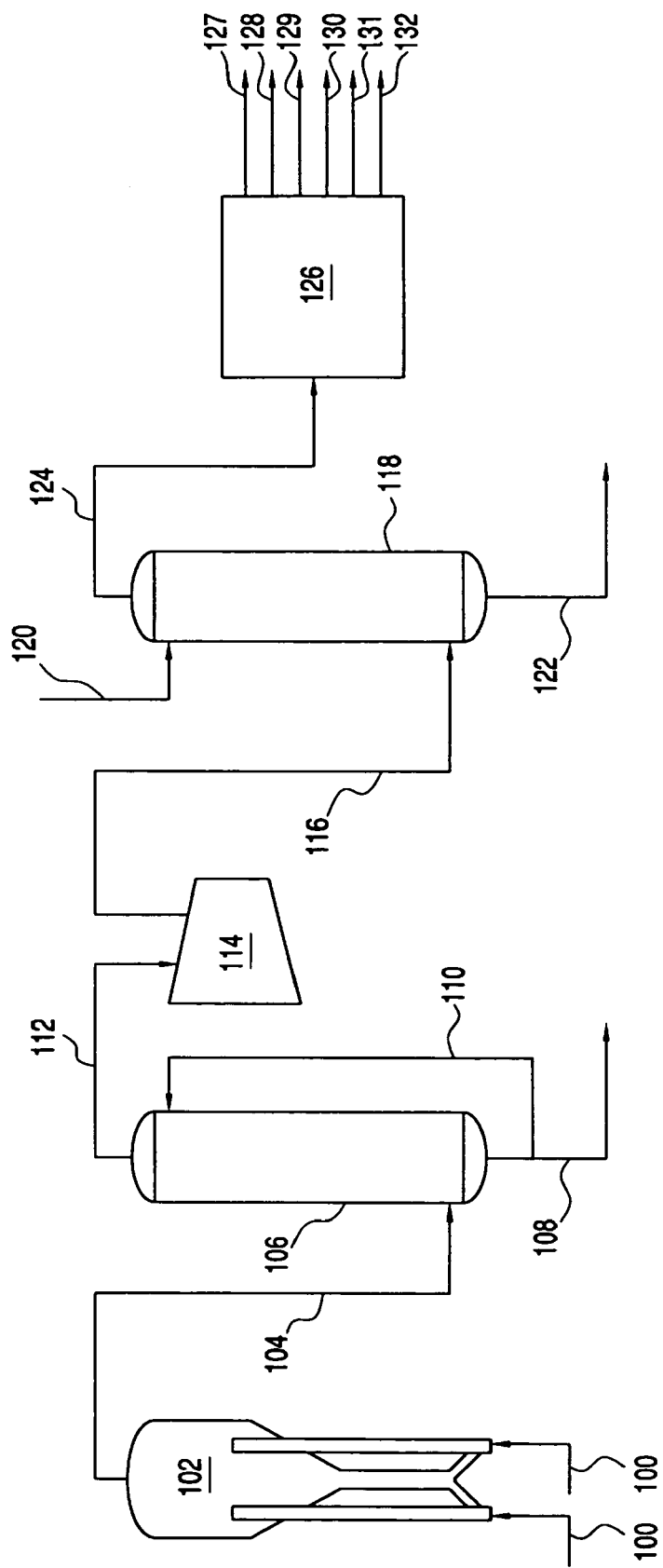
FIG. 1 presents a flow diagram illustrating an oxygenate to olefin reaction unit and an effluent processing system.

The present invention provides improved fluidization processes for fluidized bed reactors, and particularly, for fast-fluidized reactors utilized in an oxygenate to olefin (OTO) reaction systems. Additionally, the present invention provides a practical use for oxygenate components and/or heavy olefins contained in an OTO reaction effluent.

One embodiment of the invention is to a novel process and reaction system for fluidizing catalyst compositions in an OTO reaction system while also increasing the amount of light olefins formed in the OTO reaction system. Specifically, in this embodiment, oxygenate components and/or C4+ olefins (heavy olefins) are introduced into the OTO reaction system to serve as the fluidizing medium. For purposes of this specification and the appended claims, a "fluidizing medium" is a gaseous composition capable of causing particulate material, e.g., catalyst particles, to behave in a fluidized manner. Preferably, the oxygenate components and/or heavy olefins are substantially dry and thus, unlike steam fluidizing mediums, will not significantly deactivate the molecular sieve catalyst compositions contained in the OTO reaction system. Additionally, as the oxygenate components and/or heavy olefins fluidize the molecular sieve catalyst compositions contained in the OTO reaction system, at least a portion of the oxygenate components and/or heavy olefins are converted to additional light olefins. As a result, an increase in light olefin production can be advantageously realized by utilizing oxygenate components and/or heavy olefins as the fluidizing medium in an OTO reaction system.

Preferably, the oxygenate components and/or heavy olefins are formed as by-products of the OTO reaction process and are yielded from the OTO reaction system with the light olefins in an OTO reaction effluent. In this embodiment, the oxygenate components and/or heavy olefins contained in the OTO reaction effluent are separated from the light olefins contained therein and are recycled to the OTO reaction system. In the OTO reaction system, the recycled oxygenate components and/or heavy olefins are utilized as a fluidizing medium for fluidizing the molecular sieve catalyst compositions in the OTO reaction system, as described above. By converting by-product oxygenate components and/or heavy olefins in an OTO reaction effluent to additional light olefins, the effective selectivity for light olefins in an OTO reaction system can be advantageously increased. In this manner, the recycled oxygenate components and/or heavy olefins act as a fluidizing medium for fluidizing catalyst compositions contained in the OTO reaction system and also increase the amount of light olefins formed in the reaction system.

In one preferred embodiment, a fluidizing medium contacts a molecular sieve catalyst composition under conditions effective to increase the selectivity of the molecular sieve catalyst composition for light olefins. In this embodiment, the molecular sieve catalyst composition optionally comprises regenerated catalyst and/or fresh catalyst. As used herein, "fresh catalyst" means a virgin catalyst composition, which has not been utilized to convert oxygenates to light olefins and which has not been regenerated. The molecular sieve catalyst composition in this embodiment optionally is introduced into the reaction system at one or more of the standpipe, the disengaging zone, and/or the standpipe entry zone of the disengaging zone.

B. Fluidizing Medium Components

In one embodiment of the present invention, an oxygenate contacts a molecular sieve catalyst composition in a fluidized reactor under first conditions effective to convert the oxygenate to light olefins. The molecular sieve catalyst composition and the light olefins are then directed to a disengaging zone. The light olefins are yielded from the disengaging zone and the molecular sieve catalyst composition is directed from the disengaging zone to a standpipe.

Optionally, the disengaging zone comprises a standpipe entry zone in which the molecular sieve catalyst composition is fluidized to facilitate transfer of the catalyst composition to the standpipe. In one or more of the standpipe, the disengaging zone and/or the standpipe entry zone, the molecular sieve catalyst composition is fluidized with a fluidizing medium comprising one or more reactive components. Ideally, the one or more reactive components can be converted, under appropriate fluidization conditions, to light olefins. The molecular sieve catalyst composition preferably is transported in a fluidized manner from the standpipe back to the fluidized reactor.

According to the present invention, the reactive component or components contained in the fluidizing medium may vary widely. In one embodiment, the fluidizing medium comprises one or more oxygenate components. Additionally or alternatively, the fluidizing medium optionally comprises one or more C4+ olefins, also referred to herein interchangeably as "heavy olefins", or "heavy olefin byproducts". Additionally or alternatively, if economic circumstances so facilitate, the reactive component in the fluidizing medium optionally comprises propylene. Additionally or alternatively, the fluidizing medium optionally comprises one or more paraffins. In a preferred embodiment, the fluidizing medium is selected from one or more of methanol, dimethyl ether, C4+ olefins, C4+ hydrocarbons, acetaldehyde, acetone, butanone, acetic acid and mixtures thereof. In one preferred embodiment, the one or more oxygenates, heavy olefins and/or paraffins contained in the fluidizing medium are byproducts of the OTO reaction process.

As used herein, an "oxygenate" or "oxygenated compound" is a molecule containing at least one oxygen atom, at least one carbon atom and at least two hydrogen atoms. A non-limiting list of exemplary oxygenates includes: formaldehyde, ethanal, propanal, butanal, pentanal and higher aldehydes; acetone, butanone, pentanone, hexanone and higher ketones; dimethyl ether, methyl ethyl ether, diethyl ether, ethyl propyl ether and higher ethers; unsaturated species thereof, e.g., crotonaldehyde; formic acid, acetic acid, propionic acid, butanoic acid and higher carboxylic acids.

An "olefin," as used herein, is an at least partially unsaturated molecule that does not contain oxygen. Thus, "C4 olefins" means at least partially unsaturated molecules that do not contain oxygen and which contain exactly 4 carbon atoms, e.g., 1-butene, 2-butene, and butadiene. "C4+ olefins" means at least partially unsaturated molecules that do not contain oxygen and which contain 4 or more carbon atoms.

As used herein, a "paraffin" is a fully saturated molecule containing carbon and which does not contain oxygen. Thus, "C4 paraffins" means fully saturated molecules containing carbon, not containing oxygen, and containing exactly 4 carbon atoms. "C4+ paraffins" means fully saturated molecules that do not contain oxygen and which contain 4 or more carbon atoms. For purposes of this specification and the appended claims, the terms "hydrocarbons" and "paraffins" are synonymous, and are interchangeably used herein.

The types of oxygenate compounds that may be included in the fluidizing medium include alcohols, aldehydes, ketones, esters, acids and ethers in the C1 to C6 range. Preferred oxygenate components contained in the fluidizing medium include methanol, ethanol and dimethyl ether.

A reaction effluent from an OTO reaction system may contain many oxygenates, and, in one embodiment, the fluidizing medium comprises one or more of these oxygenates. Specifically, an OTO reaction effluent can include one or more of the following oxygenates: Dimethyl Ether (DME), Methyl Ethyl Ether, Methyl Isopropyl Ether, Acetaldehyde, Methyl Sec-Butyl Ether, n-Propanal, 2-Propenal, 2-Methyl-2-Propenal, iso-Butanal, Butanal, Acetic Acid, Methyl Ester, Methanol, Acetone, 2-Methyl Butanal, Propanoic Acid, Methyl Ester, 3-Buten-2-one, Ethanol, 2-Butanone, iso-Propanol, 3-Methyl-3-Buten-2-one, Pentanal, 2-Methyl Pentanal, 3-Methyl Pentanal, 3-Methyl-2-Butanone, 3-Pentanone, 2-Methyl-1-Penten-3-one, 2-Pentanone, 2-Methyl-3-Pentanone, 3-Methyl-2-Pentanone, 4-Methyl-2-Pentanone, Formic Acid, Acetic Acid, Propanoic Acid, and Butyric Acid.

The fluidizing medium may or may not comprise the principal oxygenate, by weight, that is separately fed to the fluidized reactor. For example, if the principal oxygenate that is fed to the fluidized reactor comprises methanol, the fluidizing medium may or may not comprise methanol. In one embodiment, the fluidizing medium comprises the principal oxygenate in an amount less than about 10.0, less than about 5.0, or less than about 1.0 weight percent, based on the total weight of the fluidizing medium fed to the fluidization site. The fluidizing medium optionally further comprises one or more relatively inert components (e.g., nitrogen), other oxygenate compounds, heavy olefins, propylene, and/or paraffins.

The amount of oxygenate components that are contained in the fluidizing medium may vary widely. In one embodiment, there are no oxygenates. In other embodiments, there is less than about 5.0, less than about 3.0, less than about 1.0, or less than about 0.5 wt. % oxygenates, based on the total weight of all fluidizing media fed to the fluidization site, including non-byproducts such as steam, if any. In additional embodiments, there is at least about 0.1, at least about 1.0, at least about 10.0, or at least about 30.0 wt. % oxygenates. In still other embodiments, there are at least about 0.1 wt. % and no greater than about 80 wt. %, or at least about 0.1 wt. % and no greater than about 50 wt. % oxygenates, or at least about 0.5 wt. % and no greater than about 30 wt. % oxygenates.

Similarly, the types of heavy olefins that may be included in the fluidizing medium may vary widely. Preferably, the fluidizing medium comprises one or more heavy olefins in the C4 to C8 range, most preferably C4 olefins. Preferred heavy olefin components contained in the fluidizing medium include: 1-butene; 2-butene; isobutylene; 1,2-butadiene; 1,3-butadiene; 1-butyne; 2-butyne; 1-pentene; 2-pentene; and pentadiene in one or more isomers.

Oxygenate and heavy olefin byproducts formed in an OTO conversion process generally are less reactive than the principal oxygenate in an oxygenate-containing feedstock that is directed to an OTO reaction system. As a result, the conditions in the fluidized reactor of an OTO reaction system, which are ideally suited for converting the principal oxygenate to light olefins, are not particularly favorable for converting the oxygenate or heavy olefin byproducts to light olefins. However, the conditions in the standpipe (and possibly in the standpipe entry zone) provide exposure to the catalyst compositions at a much lower WHSV than in the fluidized reactor of the OTO reaction system. Temperature conditions are also preferably higher in the standpipe (or standpipe entry zone) than in the fluidized reactor. Accordingly, conditions in the standpipe (or standpipe entry zone) may be particularly favorable for converting oxygenate or heavy olefin byproducts to light olefins. Further, given the lack of water-forming oxygen atoms, heavy olefins are particularly well-suited for use as a fluidizing medium.

For similar reasons, dimethyl ether (DME) is a preferred oxygenate for the fluidizing medium. DME is another effective reactive component for catalyst fluidization in that it too has a lower reactivity than methanol, typically the preferred oxygenate for OTO conversion processes, although it is more reactive than heavy olefins. Additionally, the amount of DME formed in an OTO reaction system advantageously is on the order of the amount of fluidizing medium required for effective catalyst fluidization. Further, one mole of DME will produce one less mole of water in the manufacture of olefins than the comparable two moles of methanol. Thus, it may be desired to separate the DME from the OTO reaction effluent and recycle it to extinction to the OTO reaction system as the fluidizing medium.

If the fluidizing medium comprises DME, the fluidizing medium optionally comprises DME in an amount less than about 5.0, less than about 3.0, less than about 1.0, or less than about 0.5 wt. %, based on the total weight of all fluidizing media fed to the fluidization site, including non-byproducts such as steam, if any. In additional embodiments, there is at least about 0.1, at least about 1.0, at least about 10.0, or at least about 30.0 wt. % DME. In still other embodiments, there is at least about 0.1 wt. % and no greater than about 80 wt. %, or at least about 0.1 wt. % and no greater than about 50 wt. % DME, or at least about 0.5 wt. % and no greater than about 30 wt. % DME.

A reaction effluent from an OTO reaction system may contain several heavy olefins, and, in one embodiment, the fluidizing medium comprises one or more of these heavy olefins. Specifically, an OTO reaction effluent can include one or more of the following heavy olefins: 1-butene, 2-butene, isobutene, butadiene, $C_5$ olefins, $C_5$ diolefins, $C_6$ olefins or diolefins, and $C_7+$ olefins or diolefins, and aromatics such as benzene, toluene, xylene, C9 aromatics, especially methyl and ethyl substituted aromatics, and heavier aromatics, including durene and hexamethyl benzene, and dual ring aromatics such as naphthlene and biphenyl.

The amount of heavy olefins that are contained in the fluidizing medium may vary widely. In one embodiment, there are no heavy olefins. In other embodiments, there is at least about 1.0, or at least about 10.0, or at least about 30.0, or at least about 50.0 wt. % heavy olefins, based on the total weight of all fluidizing media fed to the fluidization site, including non-byproducts such as steam, if any. In other embodiments, there is at least about 1.0 wt. % and no greater than about 99 wt. %, or at least about 5.0 wt. % and no greater than about 98.0 wt. % oxygenates, or at least about 10.0 wt. % and no greater than about 98.0 wt. % oxygenates.

In order to provide a fluidizing medium that has desired reactivity characteristics, it may be desirable to include paraffins, which are generally unreactive, in the fluidizing medium. The types of paraffins that may be included in the fluidizing medium may vary widely. Preferably, the fluidizing medium comprises one or more paraffins in the C1 to C8 range.

A reaction effluent from an OTO reaction system may contain several paraffins that could be included in the fluidizing medium. In one embodiment, the fluidizing medium comprises one or more of these paraffins.

The amount of paraffins that are contained in the fluidizing medium may vary widely. In one embodiment, there are no paraffins. In other embodiments, there is at least about 0.1, or at least about 1.0, or at least about 3.0, or at least about 5.0 wt. % paraffins, based on the total weight of all fluidizing media fed to the fluidization site, including non-byproducts such as steam, if any. In additional embodiments, there is no greater than about 50.0, or no greater than about 20.0, or no greater than about 10.0 wt. % paraffins. In other embodiments, there is at least about 0.1 wt. % and no greater than about 99.0 wt. %, or at least about 0.1 wt. % and no greater than about 30.0 wt. %, or at least about 1.0 wt. % and no greater than about 20.0 wt. % paraffins.

In one embodiment, the fluidizing medium comprises both heavy olefins and oxygenates, optionally heavy olefin and oxygenate byproducts formed in an OTO conversion process, over a wide range of proportions. In varying manifestations of the present invention, the proportion of heavy olefins is at least about 10 wt %, or at least about 50 wt. %, or at least about 80 wt. %, or at least about 90 wt. %, or at least about 95 wt. %, based on the total weight of only all heavy olefins and oxygenates fed to the fluidization site, exclusive of other components as steam. In an alternate manifestation, the proportion of heavy olefins is at least about 10 wt % and no greater than about 99 wt. %.

Due to the hydrothermal instability of the catalysts typically utilized in OTO reaction processes, the fluidizing medium preferably is substantially dry. However, it is contemplated that the fluidizing medium of the present invention may include a minimal amount of water, optionally in the form of steam. If the fluidizing medium comprises water or steam, then the fluidizing medium preferably comprises less than about 99 wt. %, more preferably less than about 90 wt. %, more preferably less than about 75 wt. %, still more preferably less than about 50 wt %, yet more preferably less than about 30 wt. %, and most preferably less than about 10 wt. % steam, based on the total weight of all fluidizing media fed to the fluidization site.

In one embodiment, the fluidizing medium is directed to a drying unit prior to introduction into the reaction system. In the drying unit, the water contained in the fluidizing medium is selectively removed therefrom, e.g., by absorption or adsorption. Preferably, the drying unit contains molecular sieves and operates as an adsorption unit, which selectively removes water molecules from the fluidizing medium. Optionally, the molecular sieves can be regenerated to remove the water molecules therefrom through well-known techniques. After the molecular sieves are regenerated they optionally are redirected to the drying unit to remove additional water from the fluidizing medium.

If the desired fluidizing medium comprises one or more byproducts of the OTO reaction system, it is desirable to separate the light olefins from the byproducts contained in the OTO reaction effluent prior to sending the byproducts to the OTO reaction system to serve as the fluidizing medium. Thus, in one embodiment, the process of the invention comprises a step of separating an OTO effluent stream into a first fraction and a second fraction. The first fraction comprises a weight majority, preferably at least 75 weight percent, and most preferably at least 90 weight percent of the light olefins that were contained in the effluent stream. The second fraction comprises a weight majority, preferably at least 75 weight percent, and most preferably at least 90 weight percent of the byproducts that were contained in the effluent stream. In this embodiment, all or a portion of the second fraction is reintroduced into the OTO reaction system to serve as the fluidizing medium. Optionally, the second fraction is further processed to remove components that are undesirable for reintroduction into the OTO reaction system.

As indicated above, it may be undesirable to send some byproducts that are formed in the OTO reaction process back to the OTO reaction process to serve as the fluidizing medium. For example, it is undesirable to send components that are liquids at fluidization conditions back to the OTO reaction system to serve as the fluidizing medium, or very heavy, non-reactive components that may build up within an overall OTO reaction and recovery process. A non-limiting list of such undesirable components includes: aromatics; C7+ paraffins. The fluidizing medium also preferably does not contain an appreciable amount (preferably less than 10 wt. %, even more preferably less than 5 wt. %) of non-oxygenate components, individually or collectively, having normal boiling points greater than 176° F. (80° C.).

C. Fluidization Sites and Conditions

1. Standpipe Fluidization

Figure 2:
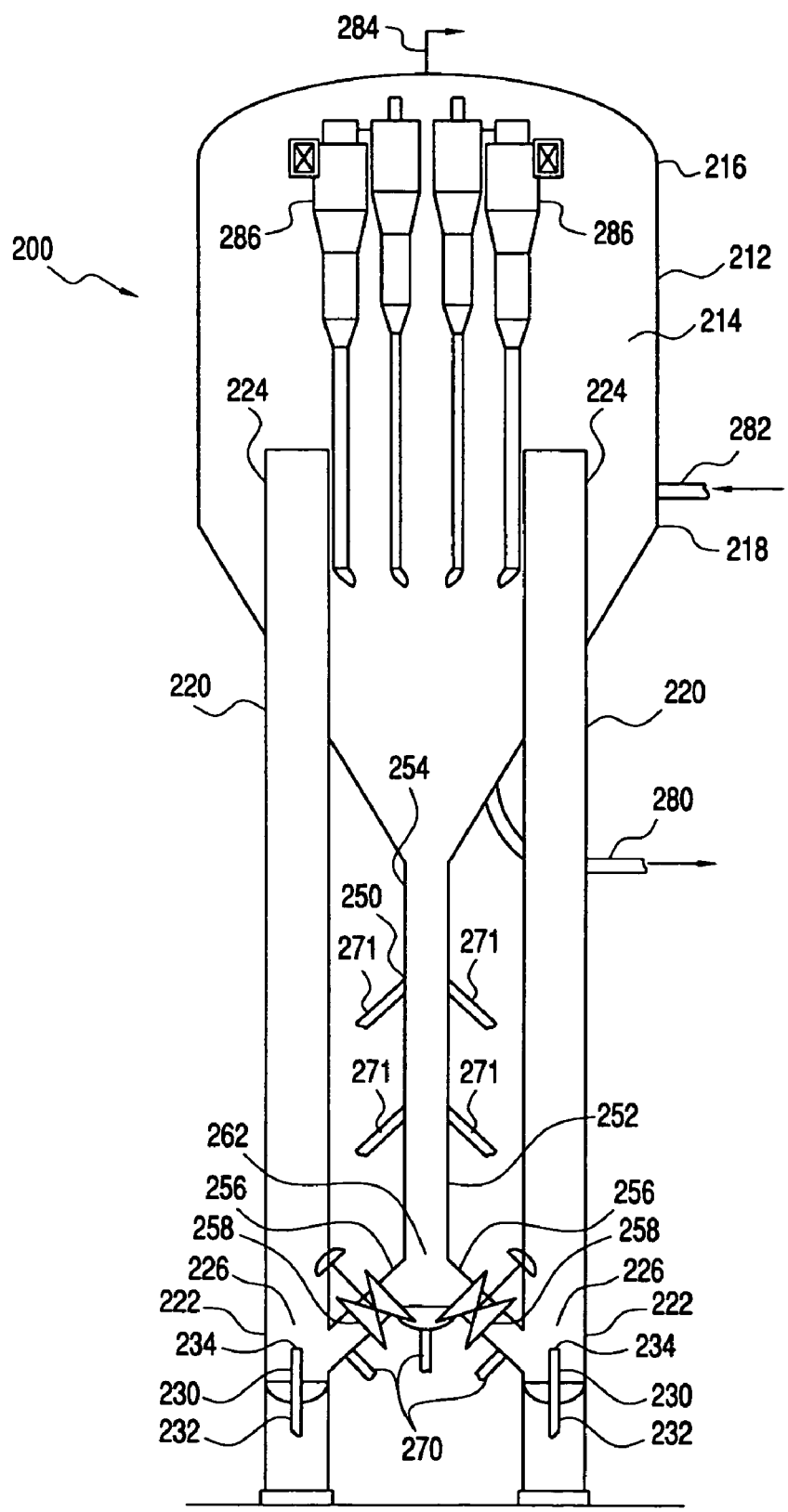
FIG. 2 presents a partial cross-sectional view of a fast-fluidized reactor, which optionally receives a fluidizing medium according to the present invention.

As indicated above, in one embodiment, the fluidization medium is introduced into a standpipe within an OTO reaction system. As used herein, a "standpipe" is any conduit that is in fluid communication between a disengaging zone and a fluidized reactor. FIG. 2 illustrates a hydrocarbon conversion apparatus, e.g., an OTO reaction unit, which includes a standpipe into which the fluidizing medium may be introduced according to one embodiment of the present invention. The apparatus, generally designated 200, comprises a shell 212, a plurality of riser reactors 220, feed distributors 230, and a catalyst return 250. As shown, the standpipe of FIG. 2 comprises catalyst return 250 and arms 256.

With continuing reference to FIG. 2, the shell 212 defines a disengaging zone 214 in which a product of the hydrocarbon conversion reaction, e.g., an OTO conversion reaction, is separated from the catalyst that catalyzes the hydrocarbon conversion reaction. Shell 212 includes a first end 216 and a second end 218.

Riser reactors 220 extend into shell 212 and the disengaging zone 214. Each riser reactor 220 includes a first end 222 into which the catalyst and feed are fed to conduct the hydrocarbon conversion reaction. Each riser reactor 220 further includes a second end 224 through which the catalyst, product, and unreacted feed, if any, exit the riser reactor 220. The first end 222 of each riser reactor 220 terminates in a mouth 226 through which the catalyst and feed are fed into the riser reactor 220.

With continuing reference to FIG. 2, to provide a feed to the riser reactors 220, at least one feed distributor 230 is positioned near the first ends 222 of the riser reactors 220. More than one feed distributor 230 may be employed to provide feed in various states, e.g., one feed distributor 230 may provide feed in a vapor form while a second feed distributor 230 may provide feed in a liquid form. Each feed distributor includes a body, not shown, from which at least one neck 232 extends. Each riser reactor 220 has at least one associated neck 232. Each feed distributor 230 terminates in a head 234. Each head 234 is positioned adjacent to the first end 222 of each riser reactor 220. Desirably, each head 234 extends upwardly into each riser reactor 220. More desirably, each head 234 is positioned at or above the mouth 226 of the first end 222 of each riser reactor 220. Feed distributor 230 may include an optional flow control device, not shown, positioned on feed distributor 230 to provide an equal amount of feed to each head 234. The flow control device can also be employed to measure flow as well. Further, a nozzle, not shown, may be positioned on each head 234 to further control the distribution of the feed to each riser reactor 220. Additionally, each head 234 may be fitted with screening device, not shown, to prevent back flow of catalyst into any of the feed distributors 230.

In the hydrocarbon conversion apparatus 200 shown in FIG. 2, a single catalyst return 250 is positioned centrally in relation to the riser reactors 220. The catalyst return 250 provides fluid communication between the disengaging zone 214 of the shell 212 and the riser reactors 220. The catalyst return 250 has a first end 252 and a second end 254. The first end 252 of the catalyst return 250 opens into catalyst retention zone 262, and the second end 254 of catalyst return 250 opens to the disengaging zone 214. A series of arms 256 are positioned on the first end 252 of the catalyst return 250. The arms 256 extend from the catalyst return 250 to each of the riser reactors 220 and provide fluid communication between the catalyst return 250 and the riser reactors 220. The number of arms 256 will correspond to the number of riser reactors 220 with each riser reactor 230 having at least one corresponding arm 256. The catalyst return 250 is provided to transport catalyst from the disengaging zone 214 of shell 212 to the first ends 222 of the riser reactors 220. Flow of catalyst through the catalyst return 250 may optionally be controlled through the use of a flow control device 258 positioned on the catalyst return 250 or on each arm 256. The flow control device(s) 258 can be any type of flow control devices currently in use in the art to control catalyst flow through catalyst transfer lines. If employed, the flow control device 258 is desirably a ball valve, a plug valve or a slide valve.

In the embodiment shown in FIG. 2, the first end 252 of the catalyst return 250 and the arms 256 define a catalyst retention zone 262. The arms 256 of the catalyst return 250 open to the catalyst retention zone 262. The catalyst retention zone 262 is provided to retain catalyst that is used to catalyze the hydrocarbon conversion reaction which is conducted in the apparatus 200. As one of skill in the art will appreciate, the boundary between the catalyst retention zone 262 and the catalyst return 250 is fluid and depends, at least in part, on the level of catalyst contained in the catalyst retention zone 262 and the arms 256 of the catalyst return 250.

At least one fluidizing medium nozzle 270 is positioned beneath the catalyst retention zone 262. A fluidizing medium of the present invention is fed through fluidizing medium nozzle 270 to fluidize a fluidizable catalyst in the catalyst retention zone 262 and the catalyst return 250. Additional fluidizing medium nozzles 271, as shown in FIG. 2, may also be positioned on the catalyst return 250 to further fluidize fluidizable catalyst contained in the catalyst return 250.

In a "bubbles-up" flow regime, the fluidizing medium flows in an upward direction while the catalyst flows in a downward direction. In a "bubbles-down" flow regime, the fluidizing medium and the catalyst flow in a downward direction, although not necessarily at the same speed. Typically, the pressure balance in the reaction system will determine whether the fluidizing medium will behave in a bubbles-up or bubbles-down flow regime. By angling the fluidizing medium nozzles 271 with respect to an imaginary horizontally-extending plane, however, a localized bubbles up or bubbles down flow regime can be created. As used herein, "horizontal" means a direction parallel to grade.

Thus, in one embodiment, shown in FIG. 2, the fluidizing medium nozzles 271 situated on the catalyst return 250 are angled in an upward direction with respect to an imaginary horizontal plane, as shown in FIG. 2. By situating the fluidizing medium nozzles 271 in this angled manner, the fluidizing medium that is introduced into the hydrocarbon conversion apparatus 200 via fluidizing medium nozzles 271 may assist in creating a superficial gas velocity (SGV) in an upward direction. In operation, catalyst is transported in a downward direction through standpipe 250 although the pressure balance and the orientation of the fluidizing medium nozzles 271 creates a SGV in an upward direction. Regardless of how it is achieved, in certain embodiments, the SGV ranges from about 0.1 to about 1.0 m/s, preferably from about 0.2 to about 0.8 m/s in an upward direction. Ideally, the mass flux of the catalyst composition in a downward direction is less than about 50 lb/ft$^2$-s (244 kg/m$^2$-s).

To determine the SGV of reactive material in the standpipe or elsewhere, one divides the volume of reactive material fed to the standpipe, at the conditions within the standpipe, by the cross-sectional area for flow of the standpipe. To determine the mass flux of the catalyst composition, one determines the catalyst circulation rate (e.g., SGV) in the manner described above, and simply divides it by the cross-sectional area of the standpipe.

If light olefins become entrained with catalyst from the disengaging zone and enter the standpipe, the entrained light olefins may undesirably be converted to one or more secondary byproducts in the standpipe. The bubbles up catalyst flow regime is particularly preferred in that it will minimize entrainment of valuable light olefins from the OTO conversion process into the standpipe. As a result, the amount of light olefins converted to secondary byproducts in the standpipe or elsewhere in the OTO reaction system can be advantageously minimized.

Notwithstanding the above, it is within the scope of the present invention that all or any portion of the fluidizing medium and any resultant conversion products may be carried in a downward direction, co-directional with the flow of the catalyst. In one embodiment, at least a portion of the fluidizing medium and any resultant conversion products are carried in a downward direction in the standpipe (or standpipe entry zone), co-directional with the flow of the catalyst. In another embodiment, a portion of fluidizing medium and any resultant conversion products moving downward co-directionally with the catalyst is provided from a bubbles up zone in the reactor.

In another embodiment, not shown, the fluidizing medium nozzles 271 on catalyst return 250 form an angle substantially parallel to grade, as illustrated in U.S. patent application Ser. No. 09/564,613, filed May 4, 2000, the entirety of which is incorporated herein by reference. In yet another embodiment, not shown, the fluidizing medium nozzles 271 are angled in a downward direction.

The hydrocarbon conversion apparatus 200 may also include an outlet 280 through which the catalyst can be removed from the apparatus 200. The outlet 280 is shown as being positioned on the second end 218 of the shell 212 but may be positioned at any position on the apparatus 200. The apparatus 200 may also include an inlet 282 through which the catalyst may be placed into the apparatus 200. Although the inlet 282 is shown as being positioned on the second end 218 of the shell 212, the inlet 282 may be positioned at any position on the apparatus 200. A line 284 is provided to remove products from the apparatus 200 under pneumatic pressure.

A series of separation devices 286 are shown as being positioned in the disengaging zone 214 of shell 212. The separation devices 286 may be cyclonic separators, filters, screens, impingement devices, plates, cones or any other devices which would separate the catalyst from the product of the conversion reaction. The separation devices 286 shown in FIG. 2 are cyclonic separators.

The hydrocarbon conversion apparatus 200 which is shown in FIG. 2 functions in the following manner.

The apparatus 200 is filled with an appropriate amount of catalyst which is retained in the catalyst return 250 and the catalyst retention zone 262. The catalyst is fluidized in the catalyst return 250 and the catalyst retention zone 262 by means of a fluidizing medium which is provided to the hydrocarbon conversion apparatus 200 through fluidizing medium nozzles 270 and 271. The flow of catalyst to the riser reactors 220 can be controlled by the flow control devices 258. Feed is provided to the riser reactors 220 through the feed distributors 230.

Once the catalyst has reached an acceptable fluidized state, a feed is fed into the hydrocarbon conversion apparatus 200 through necks 232. The feed passes through the necks 232 and exits through the heads 234 thereof. The feed is distributed to each of the riser reactors 220 through their first ends 222.

A pressure differential created by the velocity of the feed entering the first ends 222 of the riser reactors 220 and the pressure of the height of fluidizable catalyst in the catalyst return(s) 250 and the catalyst retention zone 262 causes catalyst to be aspirated into the first ends 222 of the riser reactors 220. The catalyst is transported through the riser reactors 220 under well known principles in which the kinetic energy of one fluid, in this case the feed, is used to move another fluid, in this case the fluidized catalyst. The catalyst and feed travel from the first ends 222 to the second ends 224 of the riser reactors 220. As the catalyst and feed travel through the riser reactors 220, the hydrocarbon conversion reaction occurs and a conversion product is produced.

The catalyst, product and unreacted feed, if any, exit the riser reactors 220 through their second ends 224. The catalyst is separated from the product and any unreacted feed by the separation devices 286. The separated catalyst is fed to the second end 218 of shell 212 while the product and any unreacted feed are removed from the apparatus through the line 284.

A portion of the catalyst may be removed from the apparatus 200 through the outlet 280 and sent to a regeneration apparatus, not shown, or removed entirely from the apparatus 200. The regenerated catalyst is returned to the apparatus 200 through the inlet 282. Optionally, the regenerated catalyst is introduced at a standpipe entry zone, discussed in detail with reference to FIG. 3, to the standpipe or to the disengaging zone, as shown in FIG. 2.

The separated catalyst enters the first end 252 of the catalyst return 250 and is recycled to be reused in the hydrocarbon conversion reaction. The catalyst is returned through the catalyst return 250 to the catalyst containment area 262 where the catalyst is maintained in a fluidized state by the fluidizing medium provided through the fluidizing medium nozzles 270 and 271.

2. Inter-Vessel Fluidization

In one embodiment, the fluidizing medium optionally operates to transport the OTO catalyst composition in a fluidized manner between two or more vessels contained in the OTO reaction system. In this embodiment, the fluidizing medium contacts the molecular sieve catalyst composition under conditions effective to fluidize the molecular sieve catalyst composition in one or more of a plurality of conduits in an OTO reaction system. In this embodiment, the invention comprises a step of providing a reaction system comprising a fluidized reactor and a disengaging zone, and further comprising one or more of a stripping unit, a catalyst regenerator, a catalyst cooler, a standpipe, a standpipe entry zone and a plurality of conduits for transporting a molecular sieve catalyst composition between these units. An oxygenate contacts the molecular sieve catalyst composition in the fluidized reactor under first conditions effective to convert the oxygenate to light olefins and optionally one or more byproducts. The molecular sieve catalyst composition, the light olefins, and the optional by-products are directed to a disengaging zone, from which the light olefins are yielded. The molecular sieve catalyst composition is directed from the disengaging zone to a standpipe. The molecular sieve catalyst composition is directed from the standpipe to the fluidized reactor.

In one embodiment, the molecular sieve catalyst composition contacts a fluidizing medium in one or more of the plurality of conduits under second conditions effective to transport the molecular sieve catalyst composition in a fluidized manner through the one or more of the plurality of conduits. The fluidizing medium preferably is selected from one or more of methanol, dimethyl ether, C4+ olefins, C4+ hydrocarbons, acetaldehyde, acetone, butanone, acetic acid byproducts of an OTO conversion process or a mixture thereof, although any of the fluidizing mediums discussed above can be used. Optionally, a superficial gas velocity of from about 0.1 to about 1.0 m/s, preferably from about 0.2 to about 0.8 m/s, is formed in the one or more of the plurality of conduits, further optionally in an upward direction.

Optionally, the one or more of the plurality of conduits comprises a conduit in fluid communication between the disengaging zone and the stripping unit. Additionally or alternatively, the one or more of the plurality of conduits comprises a conduit in fluid communication between the stripping unit and the catalyst regenerator. Additionally or alternatively, the one or more of the plurality of conduits comprises a conduit in fluid communication between the catalyst regenerator and the catalyst cooler. Additionally or alternatively, the one or more of the plurality of conduits comprises a conduit in fluid communication between the catalyst regenerator and the fluidized reactor. Additionally or alternatively, the one or more of the plurality of conduits comprises a conduit in fluid communication between the catalyst regenerator and a standpipe entry zone, discussed below with reference to FIG. 3. Additionally or alternatively, the one or more of the plurality of conduits comprises a conduit in fluid communication between the catalyst cooler and the fluidized reactor. Additionally or alternatively, the one or more of the plurality of conduits comprises a conduit in fluid communication between the disengaging zone and the fluidized reactor. Optionally, the fluidizing medium contacts the molecular sieve catalyst composition in the one or more of the plurality of conduits under second conditions effective to convert at least a portion of the fluidizing medium to additional light olefins.

Figure 3:
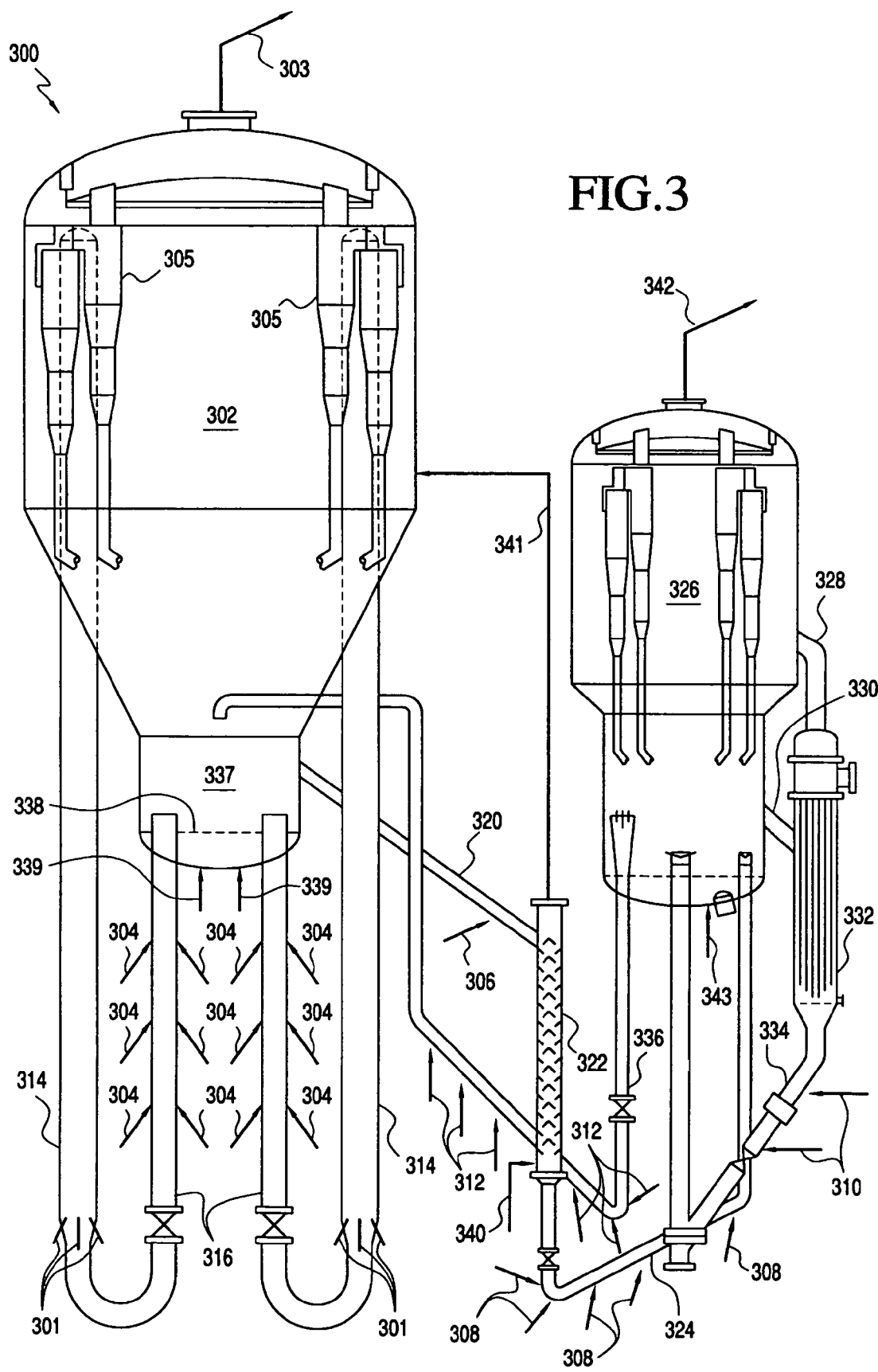
FIG. 3 presents a flow diagram illustrating an oxygenate to olefin reaction unit and a catalyst stripping and regeneration system with various fluidization zones for receiving a fluidizing medium according to the present invention.

One non-limiting embodiment of this aspect of the present invention is illustrated in FIG. 3, which illustrates an OTO reaction system, generally designated 300. The OTO reaction system 300 comprises a fluidized reactor 314 (two are shown), a disengaging zone 302, a catalyst stripper 322, a catalyst regenerator 326, a catalyst cooler 332 and conduits connecting these units to one another.

In operation, an oxygenate-containing feedstock is introduced into the fluidized reactor 314 via feed nozzles 301. In the fluidized reactor 314, the oxygenate contacts a molecular sieve catalyst composition in a fast-fluidized manner under conditions effective to convert the oxygenate to light olefins. The molecular sieve catalyst composition, the light olefins and optionally unreacted feedstock are released from the fluidized reactor 314 into disengaging zone 302. In disengaging zone 302, the molecular sieve catalyst compositions are separated from the light olefins, as described in detail above with reference to FIG. 2. The light olefins are yielded from the disengaging zone 302 as reaction effluent 303, and the molecular sieve catalyst compositions are transported from the disengaging zone 302 to one or more standpipes 316 (two are shown) optionally with the assistance of one or more separation devices 305.

Optionally, the disengaging zone comprises a standpipe entry zone 337, in which separated catalyst collects prior to entering the standpipes 316. In one embodiment of the present invention, fluidizing medium is introduced into the disengaging zone 302, preferably into the standpipe entry zone 337 thereof, under conditions effective to fluidize the catalyst contained therein. As shown in FIG. 3, the standpipe entry zone 337 comprises a distribution grid 338, which is comprised of a plate having two opposing major planar surfaces and a plurality of openings passing therethrough. In operation, the fluidizing medium is introduced through one or more fluidizing medium nozzles 339 into the standpipe entry zone. As shown, the fluidizing medium is introduced through fluidizing medium nozzles 339 into a volume below the distribution grid 338. The distribution grid 338 preferably distributes the fluidizing medium throughout the standpipe entry zone 337 relatively evenly. The fluidizing medium ideally causes the catalyst contained in the standpipe entry zone 337 to behave in a fluidized manner and facilitates catalyst entry into the standpipes 316. Preferably, the flow of fluidizing medium through the openings in distribution grid 338 is sufficient to prevent a downward flow of catalyst into the volume below the distribution grid 338. Optionally, the fluidizing medium is selected from one or more of methanol, dimethyl ether, C4+ olefins, C4+ hydrocarbons, acetaldehyde, acetone, butanone, acetic acid, one or more byproducts formed in the oxygenate to olefin conversion reaction, or a mixture thereof.

In one embodiment, as described above, the catalyst compositions contact a fluidizing medium while in the standpipe 316 under conditions effective to cause the catalyst compositions to behave in a fluidized manner as they are transported in a downward direction through standpipe 316. Ultimately, the fluidized catalyst compositions are directed from the standpipe 316 back to the fluidized reactor 314 for further contacting with the oxygenate-containing feedstock. As shown, the fluidizing medium is introduced into the standpipe through one or more, preferably a plurality of, fluidizing medium nozzles 304. This aspect of the invention is described in detail above with reference to FIG. 2.

At least a portion of the catalyst compositions are withdrawn from the disengaging zone 302 via conduit 320. As shown, the catalyst compositions optionally are transported in a fluidized manner in conduit 320 from the disengaging zone 302 to the catalyst stripper 322, wherein the catalyst compositions contact a stripping medium, e.g., steam and/or nitrogen, under conditions effective to remove interstitial hydrocarbons from the molecular sieve catalyst compositions. As shown, stripping medium is introduced into catalyst stripper 322 via line 340, and the resulting stripped stream 341 is directed to the disengaging zone 302. The fluidizing medium preferably is introduced into conduit 320 via one or more, preferably a plurality of, fluidizing medium nozzles 306 to cause the catalyst composition to be transported in a fluidized manner through conduit 320. Preferably, the fluidizing medium nozzles 306 are angled with respect to conduit 320, as shown, to create a SGV in a direction from the disengaging zone 302 to the catalyst stripper 322.

During contacting of the oxygenate-containing feedstock with the molecular sieve catalyst composition in the fluidized reactor, the molecular sieve catalyst composition may become at least partially deactivated. That is, the molecular sieve catalyst composition becomes at least partially coked. In order to reactivate the molecular sieve catalyst composition, the catalyst composition preferably is directed to a catalyst regenerator. As shown, the stripped catalyst composition is transported in a fluidized manner from catalyst stripper 322 to catalyst regenerator 326 via conduit 324. The fluidizing medium preferably is introduced into conduit 324 via one or more, preferably a plurality of, fluidizing medium nozzles 308 to cause the catalyst composition to be transported in a fluidized manner through conduit 324. Preferably, the fluidizing medium nozzles 308 are angled with respect to conduit 324, as shown, to create a SGV in a direction from the catalyst stripper 322 to the catalyst regenerator 326.

In catalyst regenerator 326, the stripped catalyst compositions contact a regeneration medium, preferably comprising air and/or oxygen, under conditions effective (preferably including heating the coked catalyst) to at least partially regenerate the catalyst compositions contained therein. As shown, the regeneration medium is introduced into the catalyst regenerator 326 via line 343, and the resulting regenerated catalyst compositions are ultimately transported in a fluidized manner from catalyst regenerator 326 back to the disengaging zone 302 via conduit 336. The gaseous combustion products are released from the catalyst regenerator 326 via flue gas stream 342. In other embodiments, not shown, the regenerated catalyst is transported from the catalyst regenerator 326 to the standpipe entry zone 337 of the disengaging zone 302, to the standpipe(s) 316, or directly to the fluidized reactors 314. The fluidizing medium preferably is introduced into conduit 336 via one or more, preferably a plurality of, fluidizing medium nozzles 312 to cause the regenerated catalyst composition to be transported in a fluidized manner through conduit 336. Preferably, the fluidizing medium nozzles 312 are angled with respect to conduit 336, as shown, to create a SGV in a direction from the catalyst regenerator 326 to the disengaging zone 302. In other embodiments, not shown, the regenerated catalyst composition optionally additionally or alternatively is directed, optionally in a fluidized manner, from the catalyst regenerator 326 to one or more of the fluidized reactor 314 and/or the catalyst stripper 322. In one embodiment, not shown, a portion of the catalyst composition in the reaction system 300 is transported directly, e.g., without first passing through the catalyst stripper 322, optionally in a fluidized manner, from one or both of the fluidized reactor 314 and/or the disengaging zone to the catalyst regenerator 326.

As the catalyst composition contacts the regeneration medium in catalyst regenerator 326 the temperature of the catalyst composition will increase due to the exothermic nature of the regeneration process. As a result, it may be desirable to control the temperature of the catalyst composition by directing at least a portion of the catalyst composition from the catalyst regenerator 326 to a catalyst cooler 332. As shown, the catalyst composition is transported in a fluidized manner from catalyst regenerator 326 to the catalyst cooler 332 via conduits 330 and/or 328. The fluidizing medium optionally is introduced into one or both of conduits 330 and/or 328 via one or more, preferably a plurality of, fluidizing medium nozzles, not shown, to cause the catalyst composition to be transported in a fluidized manner through one or both of conduits 330 and/or 328. Preferably, the fluidizing medium nozzles are angled with respect to one or both of conduits 330 and/or 328, to create a SGV in a direction from the catalyst regenerator 326 to the catalyst cooler 332. In the catalyst cooler 332, the catalyst composition from the catalyst regenerator 326 contacts a cooling medium, directly or indirectly, under conditions effective to form a cooled catalyst composition.

In one embodiment, the fluidizing medium is introduced into the catalyst cooler 332 for conversion of the fluidizing medium to light olefins. In this embodiment, the catalyst cooler preferably is in fluid communication with a region of an OTO conversion area, for example as shown in U.S. Pat. No. 6,166,282, the entirety of which is incorporated herein by reference.

The resulting cooled catalyst composition is transported in a fluidized manner from catalyst cooler 332 back to the catalyst regenerator 326 via conduit 334. The fluidizing medium optionally is introduced into conduit 334 via one or more, preferably a plurality of, fluidizing medium nozzles 310 to cause the catalyst composition to be transported in a fluidized manner through conduit 334. Preferably, the fluidizing medium nozzles are angled with respect to conduit 334 to create a SGV in a direction from the catalyst cooler 332 to the catalyst regenerator 326. In other embodiments, not shown, the cooled catalyst composition optionally additionally or alternatively is directed, optionally in a fluidized manner, from the catalyst cooler 332 to one or more of the fluidized reactor 314, the disengaging zone 302, and/or the catalyst stripper 322.

It should be noted that the locations of fluidizing media discussed above are illustrative of the scope of the present invention, and that many combinations and configurations of the various equipment and conduits are possible. Further, it should be noted that, in general, using oxygenates or heavy olefins as a fluidizing medium in conduits with a net flow of vapor to the catalyst regenerator is not preferred, as combustion of the byproducts and any valuable conversion products may result. In particular, for this reason, relating to the example of FIG. 3, the use of byproducts in nozzles 308 or 310 is not a preferred embodiment.

In one particularly preferred embodiment of the present invention, the regenerated catalyst composition, or a portion thereof, is fluidized under conditions effective to increase the percent selectivity of the regenerated catalyst for converting the oxygenate in the oxygenate-containing feedstock to light olefins. As used herein, the "percent selectivity" of a catalyst composition for converting a reactive feedstock specie i, e.g., methanol, to a specified product specie j, e.g., light olefins, is defined as the weight of j formed divided by the weight of i converted, multiplied by 100. The "percent conversion" of a reactive feedstock specie i is the weight of i converted divided by the weight of i fed to the reaction system, multiplied by 100. "Percent yield" of a specified product specie j is the weight of product specie j divided by the weight of reactive feedstock specie i fed to the reaction system, multiplied by 100.

In one embodiment of this aspect of the invention, the invention comprises a step of contacting an oxygenate with a first molecular sieve catalyst composition in a fluidized reactor under first conditions effective to convert the oxygenate to light olefins and optionally one or more by-products. The first molecular sieve catalyst composition, the light olefins, and the by-products are directed to a disengaging zone, from which the light olefins are yielded. The first molecular sieve catalyst composition is directed from the disengaging zone to a standpipe. A second molecular sieve catalyst composition is added to one or more of the disengaging zone (e.g., to the standpipe entry zone thereof) and/or to the standpipe. The second molecular sieve catalyst composition contacts a fluidizing medium under second conditions effective to increase the selectivity of the second molecular sieve catalyst composition for light olefins. The first and second molecular sieve catalyst compositions are directed in a fluidized manner through the standpipe and back to the fluidized reactor.

Preferably, the second molecular sieve catalyst composition comprises regenerated catalysts. Additionally or alternatively, the second molecular sieve catalyst composition comprises fresh catalyst. As used herein, "fresh catalyst" means a virgin catalyst composition, which has not been utilized to convert oxygenates to light olefins, and which has not been regenerated. In either case, the second catalyst is pre-coked with low value materials (e.g., the fluidizing medium) to provide for better selectivity when exposed to the oxygenate in the oxygenate-containing feedstock. Optionally, the fluidizing medium is selected from one or more of methanol, dimethyl ether, C4+ olefins, C4+ hydrocarbons, acetaldehyde, acetone, butanone, acetic acid, byproducts of the OTO conversion process, or a mixture thereof.

Preferably, in this embodiment, the fluidizing medium comprises heavy olefins. Heavy olefins are preferred in this embodiment because the regenerated catalyst composition from the catalyst regenerator has an increased heat content as a result of the regeneration process. Due to this increased heat content, as the regenerated catalyst is introduced into the standpipe or other fluidization site, exposure of the heavy olefins to the regenerated catalyst will occur at a higher temperature than is typical in the standpipe. As a result, increased conversion of the heavy olefins to light olefins can be advantageously realized in addition to the increase in selectivity of the regenerated catalyst for light olefins.

In this embodiment, the first and second molecular sieve catalyst compositions are transported in a downward direction while in the standpipe, and the fluidizing medium optionally creates a SGV in an upward direction in the standpipe. The SGV preferably is from about 0.1 to about 1.0 m/s, preferably from about 0.2 to about 0.8 m/s. Alternatively, the fluidizing medium creates a SGV in a downward direction, co-directional with the flow of catalyst.

Optionally, the fluidizing medium contacts the first molecular sieve catalyst composition and/or the second molecular sieve catalyst composition during contacting with the fluidizing medium and/or during the step of directing the first and second molecular sieve catalyst composition back to the fluidized reactor under conditions effective to convert at least a portion of the fluidizing medium to additional light olefins. Thus, this aspect of the invention provides a synergistic benefit in that the fluidization of regenerated and/or fresh catalyst with the fluidizing medium increases the selectivity of the regenerated catalyst and/or the fresh catalyst and also causes a portion of the fluidizing medium to be converted to additional light olefins.

Preferably, the first molecular sieve catalyst composition and/or the second molecular sieve catalyst composition comprises a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, intergrown forms thereof, and mixtures thereof.

3. Fluidization Conditions

A variety of fluidization conditions are possible according to the present invention. As used herein, "fluidization conditions" means the physical conditions of the environment and the fluidizing medium at a fluidization site when the fluidizing medium is introduced to the fluidization site. A "fluidization site" is a location in a reaction system into which a fluidizing medium is introduced to cause a catalyst composition contained in the location to behave in a fluidized manner. A "fluidization zone" is a region in a reaction system wherein a catalyst composition is transported in a fluidized manner by the fluidizing medium.

In a preferred embodiment of the present invention, the fluidization conditions are sufficient to cause at least a portion of the reactive components contained in the fluidizing medium to be converted to light olefins, or other desired products, when the fluidizing medium contacts the fluidizing medium. Ideally, the conversion of the reactive components to light olefins, or other desired products, occurs at the fluidization site in addition to the region of the reaction system wherein the catalyst composition is transported in a fluidized manner by the fluidizing medium. Alternatively, the conditions may be not be favorable for the conversion of the reactive components to product at the fluidization site, but the conditions are favorable for such a conversion in at least a portion of the reaction system wherein the catalyst composition is transported in a fluidized manner by the fluidizing medium. For example, the temperature of the fluidizing medium may increase as it fluidizes the catalyst composition, and as a result, the conditions may become more favorable for converting the reactive components contained therein to light olefins or other products as the fluidizing medium transports the catalyst composition.

The temperature of the fluidization site ideally is high enough to cause the reactive components contained in the fluidizing medium, or a portion thereof, to convert to light olefins when the reactive components contact the catalyst composition. As a result, the preferred temperature will vary depending on the reactive component that is provided in the fluidizing medium. As a broad range, the temperature at the fluidization site optionally is in the range of from about 662° F. (350° C.) to about 1832° F. (1000° C.), preferably from about 752° F. (400° C.) to about 1472° F. (800° C.), more preferably from about 842° F. (450° C.) to about 1382° F. (750° C.), yet more preferably from about 896° F. (480° C.) to about 1202° F. (650° C.). In one embodiment, the temperature at the fluidization site is within 100° F. (38° C.) of the highest temperature in the fluidized reactor.

The fluidizing medium preferably is introduced into the fluidization site at a sufficient superficial gas velocity to cause the catalyst composition at the fluidization site to behave in a fluidized manner. The precise injection velocity may vary widely depending on the physical characteristics, e.g., density, of the components contained within the fluidizing medium as well as the physical characteristics, e.g., size and weight, if the catalyst compositions implemented in the OTO reaction system.

Optionally, the temperature of the fluidizing medium prior to introduction into the fluidization sites is less than the temperature within the fluidization site so that upon introduction into the fluidization site, the fluidizing medium flashes into a gaseous state. The temperature of the fluidizing medium prior to introduction to the fluidization site optionally is in the range of from about 212° F. (100° C.) to about 1472° F. (800° C.), preferably from about 302° F. (150° C.) to about 932° F. (500° C.), more preferably from about 392° F. (200° C.) to about 752° F. (400° C.).

The pressure at the fluidization site ideally is on the order of the pressures required for OTO conversion processes, described in detail below. The preferred pressure at the fluidization site will vary depending on the reactive component that is provided in the fluidizing medium. As a broad range, the pressure at the fluidization site optionally is in the range of from about 1 psig (7 kpag) to about 500 psig (3345 kpag), from about 5 psig (35 kpag) to about 100 psig (690 kpag), or from about 10 psig (69 kpag) to about 30 psig (207 kpag).

Optionally, the pressure of the fluidizing medium prior to introduction into the fluidization sites is greater than the pressure within the OTO reaction system so that upon introduction to the fluidization site, the fluidizing medium expands into a gaseous state. The pressure of the fluidizing medium prior to introduction to the fluidization site optionally is in the range of from about 1 psig (7 kpag) to about 1000 psig (6893 kpag), from about 10 psig (69 kpag) to about 500 psig (3446 kpag), or from about 15 psig (103 kpag) to about 100 psig (689 kpag).

The weight hourly space velocity (WHSV) at the fluidization site, e.g, at a point of introduction of the fluidizing medium to be converted to light olefins or other products, is defined as the total weight of the byproduct (oxygenate or heavy olefin or both, exclusive of paraffins or steam) in the fluidizing medium fed to the fluidization site per hour per weight of molecular sieve in the molecular sieve catalyst composition in the fluidization zone. The WHSV is maintained at a level sufficient to keep the catalyst composition in a fluidized state at the fluidization site. By definition, the fluidization zone cannot be the oxygenate conversion zone.

One can determine the WHSV of the reactive material (byproduct oxygenate or heavy olefin or both, exclusive of paraffins or steam) in the fluidizing medium introduced to a fluidization zone by many methods well known to the skilled artisan. Preferably, the rate at which the reactive material in the fluidizing medium is introduced to the fluidization site is determined using a flow meter, e.g., an orifice meter or a mass flow meter such as a coriolis meter. One can also determine the mass of the catalyst composition in the fluidization zone by measuring the difference in pressure between the ends of the length of a fluidization zone, and dividing that difference in pressure by the length over which that difference in pressure was determined. The resulting quotient can then be multiplied by the volume within that length. Dividing the rate of reactive material in the fluidizing medium introduced to the fluidizing zone by the mass of catalyst in the fluidization zone thus provides the WHSV. One must take care to use measurements based on where the reactive material is actually introduced, as in various embodiments the reactive material may only see a portion of the catalyst in a fluidization zone of the oxygenate conversion reactor. Further, the direction of fluidization medium flow (up or down) must be considered.

The WHSV in the fluidization zone preferably is less than 5 $hr^{-1}$, less than 4 $hr^{-1}$, less than 3 $hr^{-1}$, less than 2 $hr^{-1}$, or less than 1 $hr^{-1}$. In terms of ranges, the WHSV at the fluidization site optionally is from about 0.1 $hr^{-1}$ to about 5 $hr^{-1}$, from about 1 $hr^{-1}$ to about 5 $hr^{-1}$, or from about 1 $hr^{-1}$ to about 4 $hr^{-1}$.

The conversion of the reactive components (oxygenate or heavy olefin or both) contained in the fluidizing medium to additional light olefins optionally occurs at a weight percent conversion of at least 10 percent, at least 20 percent, at least 30 percent, at least 40 percent, or most preferably at least 45 percent optionally prior to the catalyst composition entering the fluidized reactor. In terms of ranges, the weight percent conversion of the reactive components contained in the fluidizing medium optionally is from about 10 to about 70 weight percent, from about 20 to about 50 weight percent or from about 30 to about 45 weight percent.

D. OTO Reaction Systems

As indicated above, the present invention relates to fluidizing catalyst compositions in a reaction system. The present invention is particularly suited for use in an OTO reaction system, which is discussed in more detail hereinafter.

Typically, molecular sieve catalysts have been used to convert oxygenate compounds to light olefins. Silicoaluminophosphate (SAPO) molecular sieve catalysts are particularly desirable in such a conversion process, because they are highly selective in the formation of ethylene and propylene. A non-limiting list of preferable SAPO molecular sieve catalysts includes SAPO-17, SAPO-18, SAPO-34, SAPO-35, SAPO-44, the substituted forms thereof, and mixtures thereof.

The feedstock preferably contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms. Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, DME, diethyl ether or a combination thereof, more preferably methanol and DME, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as methanol to olefins (MTO). In an MTO process, a methanol-containing feedstock is converted in the presence of a molecular sieve catalyst composition into one or more olefins, preferably and predominantly, ethylene and/or propylene, referred to herein as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fluidized bed process (includes a turbulent bed process), preferably a continuous fluidized bed process, and most preferably a continuous high velocity fluidized bed process, e.g., a fast-fluidized bed.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522, and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282, and U.S. patent application Ser. No. 09/564,613 filed May 4, 2000, which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol, DME, or both, is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least about 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. In one embodiment, the conditions for converting the oxygenate to light olefins comprise a temperature of from about 204° C. to about 371° C. and a SGV of from about 0.11 to about 15 m/s. See, for example, U.S. patent application Ser. No. 09/708,753 filed Nov. 8, 2000, which is herein incorporated by reference.

E. Separating OTO Byproducts for Catalyst Fluidization

As indicated, the fluidizing medium of the present invention optionally comprises one or more byproducts of the OTO reaction process. For example, the fluidizing medium optionally comprises one or more of the oxygenate byproducts of the OTO reaction process, one or more heavy olefins formed as byproducts of the OTO reaction process, and/or one or more paraffins formed as byproducts of the OTO reaction process.

FIG. 1 shows one embodiment of the present invention in which the oxygenate components, olefins and/or paraffins to be recycled as the fluidizing medium in the OTO reaction system are formed in an OTO reaction system. In the figure, an oxygenate such as methanol is directed through line 100 to an OTO fluidized reactor 102 wherein the oxygenate is converted to light olefins and various by-products which are yielded from the fluidized reactor 102 in an olefin-containing stream in line 104. The olefin-containing stream in line 104 optionally comprises methane, ethylene, ethane, propylene, propane, various oxygenate byproducts, C4+ olefins, water and hydrocarbon components. The olefin-containing stream in line 104 is directed to a quench unit or quench tower 106 wherein the olefin-containing stream in line 104 is cooled and water and other readily condensable components are condensed.

The condensed components, which comprise water, are withdrawn from the quench tower 106 through a bottoms line 108. A portion of the condensed components are recycled through a line 110 back to the top of the quench tower 106. The components in line 110 preferably are cooled in a cooling unit, e.g., heat exchanger (not shown), so as to provide a cooling medium to cool the components in quench tower 106.

An olefin-containing vapor is yielded from the quench tower 106 through overhead stream 112. The olefin-containing vapor is compressed in one or more compressors 114 and the resulting compressed olefin-containing stream is optionally passed through line 116 to a water absorption unit 118. Methanol is preferably used as the water absorbent, and is fed to the top portion of the water absorption unit 118 through line 120. Methanol and entrained water, as well as some oxygenates, are separated as a bottom stream through line 122. The light olefins are recovered through overhead line 124. Optionally, the light olefins are sent to an additional compressor or compressors (not shown), and then are input to a separation system 126, which optionally comprises one or more separation units such as distillation columns, absorption units, and/or adsorption units.

The separation system 126 separates the components contained in the overhead line 124. Thus, separation system 126 forms a light ends stream 127, optionally comprising methane, hydrogen and/or carbon monoxide; an ethylene-containing stream 128 comprising mostly ethylene; an ethane-containing stream 129 comprising mostly ethane; a propylene-containing stream 130 comprising mostly propylene; a propane-containing stream 131 comprising mostly propane; and one or more byproduct streams, shown as line 132, comprising one or more of the oxygenate byproducts, provided above, heavy olefins, heavy paraffins, and/or absorption mediums utilized in the separation process. Separation processes that may be utilized to form these streams are well-known and are described, for example, in pending U.S. patent application Ser. Nos. 10/124,859 filed Apr. 18, 2002; Ser. No. 10/125,138 filed Apr. 18, 2002; Ser. No. 10/383,204 filed Mar. 6, 2003; and Ser. No. 10/635,410 filed Aug. 6, 2003, the entireties of which are incorporated herein by reference.

According to one preferred embodiment of the present invention, the fluidizing medium comprises all or a portion of the material in line 122. Additionally or alternatively, the fluidizing medium comprises all or a portion of the material in line 132. Optionally, the desired oxygenate components are further isolated from the material in line 132 and the fluidizing medium comprises these oxygenate components. Similarly, the desired heavy olefins contained the material in line 132 optionally are further isolated from the material in line 132, and the fluidizing medium comprises these heavy olefins. Likewise, the desired heavy paraffins contained in the material in line 132 optionally are further isolated from the material in line 132, and the fluidizing medium comprises these heavy paraffins.

Whichever components, e.g., oxygenates, heavy olefins, and/or paraffins, are desired to be included in the fluidizing medium, preferably are directed from the separation system 126 (and/or quench tower 106 and/or absorption unit 118) to a holding vessel, not shown. Once it is desired to fluidize the catalyst compositions contained in the reaction system, the fluidizing medium can be withdrawn from the holding vessel, e.g., by pumping, and be directed to the desired fluidization site or sites.

Optionally, less than about 95 weight percent, preferably less than 90 weight percent, of the byproduct reactive material (oxygenate, heavy olefin and/or paraffins) contained in the OTO reaction effluent is recovered and recycled to the OTO reaction system as a fluidizing medium. Optionally, the C4+ material (optionally including both C4+ olefins and C4+ paraffins) contained in the OTO reaction effluent is separated and recycled to the OTO reaction system as the fluidizing medium without substantial separation of C4+ olefins from C4+ paraffins contained therein. This embodiment prevents excessive build-up of unreactive C4+ paraffins in the separation system of the OTO reaction system and also eliminates the need for expensive C4+ olefin/paraffin separation facilities. In terms of lower range limits, in one embodiment, at least 5 weight percent, preferably at least 20 weight percent, of the reactive byproducts contained in an OTO reaction effluent can be recovered and recycled to the OTO reaction system as the fluidizing medium. These lower range limitations are particularly preferred for providing sufficient material in combination with a bubbles up flow regime, described above, or when regenerated catalyst is provided directly to a fluidization site, e.g., a standpipe, also as described above.

EXAMPLE

Certain oxygenate molecules representative of oxygenate byproducts of an OTO reaction were reacted over a SAPO-34 catalyst prepared by the method of Lok, et. al. in U.S. Pat. No. 4,440,871. Catalyst testing was carried out in a tubular micro flow-reactor at 450° C. Reagents were introduced into the reactor via 3-μl pulses. The reagent pulses were introduced into the reactor via He carrier gas, the flow rate of which was 72 ml/min. The total reactor pressure was kept constant at 25 psig (172 kpag). The effluent from the tubular reactor was collected and analyzed by on-line gas chromatography (Hewlett Packard 6890) equipped with a flame ionization detector. The chromatographic column used was a 150 meter, 0.25 mm (inner diameter) fused silica capillary column (Model No. Petrocol DH 150).

TABLE 1

Conversion of Exemplary Oxygenates to C1–C4 Olefins and Paraffins.

| Feed | $C_2^-$ | $C_3^-$ | $C_4^-$ | $C_{1-4}^0$ | Percent Conversion |
|---|---|---|---|---|---|
| Acetaldehyde | 42.2 | 48.7 | 4.3 | 0.8 | 55.2 |
| Acetone | 11.0 | 34.0 | 43.5 | 0.6 | 45.7 |
| Butanone[1] | 10.8 | 43.7 | 25.5 | 0.4 | 60.7 |
| Acetic Acid[2] | 3.2 | 10.4 | 29.5 | 0.0 | 100.0 |

[1] 8.7 weight percent selectivity for butadiene.
[2] 53.1 weight percent selectivity for acetone.

As indicated in Table 1, above, the oxygenates analyzed in the Example converted substantially to valuable C2 to C4 olefins. Thus, these oxygenates should prove valuable, alone or in combination, as a fluidizing medium for an OTO reaction system. However, for many oxygenates the conversion is quite low compared to a typical feed oxygenate that would be undergoing reaction in an oxygenate conversion zone of an OTO reactor, say methanol as noted above. Thus to achieve higher conversions and reduce the rate of recycle of these and other byproducts (such as C4+ olefins) having lower reactivity relative to the feed oxygenate, it is beneficial to direct them to a fluidization zone as a fluidization medium, where they will be exposed to catalyst for longer periods of time (lower WHSV) and convert more thoroughly.

Having now fully described the invention, it will be appreciated by those skilled in the art that the invention may be performed within a wide range of parameters within what is claimed, without departing from the spirit and scope of the invention.

We claim:

1. A process for producing light olefins, the process comprising the steps of:
    (a) contacting an oxygenate with a molecular sieve catalyst composition in a fluidized reactor under first conditions effective to convert the oxygenate to the light olefins;
    (b) directing the molecular sieve catalyst composition and the light olefins to a disengaging zone;
    (c) yielding the light olefins from the disengaging zone;
    (d) directing the molecular sieve catalyst composition from the disengaging zone to a standpipe;
    (e) fluidizing the molecular sieve catalyst composition in the standpipe with a fluidizing medium, wherein the fluidizing medium is selected from one or more of methanol, dimethyl ether, C4+ olefins, C4+ hydrocarbons, acetaldehyde, acetone, butanone, acetic acid, one or more byproducts formed in step (a), or a mixture thereof; and
    (f) transporting the molecular sieve catalyst composition in a fluidized manner from the standpipe back to the fluidized reactor.

2. The process of claim 1, wherein the fluidizing medium is selected from one or more of methanol, dimethyl ether, C4+ olefins, C4+ hydrocarbons, acetaldehyde, acetone, butanone, acetic acid, or a mixture thereof.

3. The process of claim 1, wherein the fluidizing medium comprises one or more byproducts formed in step (a).

4. The process of claim 3, wherein the process further comprises the steps of:
    (g) separating the one or more byproducts from the light olefins; and
    (h) directing the one or more byproducts to the standpipe.

5. The process of claim 1, wherein step (e) creates a superficial gas velocity in an upward direction.

6. The process of claim 5, wherein the molecular sieve catalyst composition is transported in a downward direction while in the standpipe.

7. The process of claim 5, wherein the superficial gas velocity is from about 0.1 to about 1.0 meters/second.

8. The process of claim 7, wherein the superficial gas velocity is from about 0.2 to about 0.8 meters/second.

9. The process of claim 1, wherein the fluidizing medium contacts the molecular sieve catalyst composition in one or both of steps (e) and (f) under second conditions effective to convert at least a portion of the fluidizing medium to additional light olefins.

10. The process of claim 9, wherein the second conditions comprise a temperature of from about 350° C. to about 1000° C. and a superficial gas velocity in an upward direction of from about 0.1 to about 1.0 m/s.

11. The process of claim 10, wherein the second conditions comprise a temperature of from about 400° C. to about 800° C. and a superficial gas velocity in an upward direction of from about 0.2 to about 0.8 m/s.

12. The process of claim 9, wherein the conversion of the at least a portion of the fluidizing medium to additional light olefins occurs at a WHSV of less than 5 hr$^{-1}$.

13. The process of claim 12, wherein the WHSV is less than 3 hr$^{-1}$.

14. The process of claim 9, wherein the conversion of the at least a portion of the fluidizing medium to additional light olefins occurs at a weight percent conversion of at least 10 percent.

15. The process of claim 14, wherein the conversion of the at least a portion of the fluidizing medium to additional light olefins occurs at a weight percent conversion of at least 30 percent.

16. The process of claim 1, wherein the first conditions comprise a temperature of from about 204° C. to about 371° C. and a superficial gas velocity of from about 0.11 to about 15 m/s.

17. The process of claim 1, wherein the process further comprises the steps of:
    (g) directing a first portion of the molecular sieve catalyst composition to a catalyst regenerator;
    (h) heating the first portion in the presence of oxygen under third conditions effective to at least partially regenerate the first portion and form regenerated catalyst; and
    (i) directing the regenerated catalyst to one or more of the disengaging zone, the standpipe, or to a standpipe entry zone.

18. The process of claim 17, wherein the process further comprises the step of:
    (j) contacting the regenerated catalyst with the fluidizing medium under conditions effective to increase the selectivity of the regenerated catalyst to light olefins.

19. The process of claim 1, wherein the fluidizing medium further comprises steam.

20. The process of claim 1, wherein the molecular sieve catalyst composition comprises a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, intergrown forms thereof, and mixtures thereof.

21. A process for producing light olefins, the process comprising the steps of:

(a) providing a reaction system comprising a fluidized reactor and a disengaging zone, and further comprising one or more of a stripping unit, a catalyst regenerator, a catalyst cooler, a standpipe, a standpipe entry zone, and a plurality of conduits for transporting a molecular sieve catalyst composition between these units;

(b) contacting an oxygenate with the molecular sieve catalyst composition in the fluidized reactor under first conditions effective to convert the oxygenate to light olefins;

(c) directing the molecular sieve catalyst composition and the light olefins to a disengaging zone;

(d) yielding the light olefins from the disengaging zone;

(e) directing the molecular sieve catalyst composition from the disengaging zone to a standpipe; and (f) directing the molecular sieve catalyst composition from the standpipe to the fluidized reactor, wherein the molecular sieve catalyst composition contacts a fluidizing medium in one or more of the plurality of conduits under second conditions effective to transport the molecular sieve catalyst composition in a fluidized manner through the one or more of the plurality of conduits, and wherein the fluidizing medium is selected from one or more of methanol, dimethyl ether, C4+ olefins, C4+ hydrocarbons, acetaldehyde, acetone, butanone, acetic acid, one or more byproducts formed in step (b), or a mixture thereof.

22. The process of claim 21, wherein the fluidizing medium is selected from one or more of methanol, dimethyl ether, C4+ olefins, C4+ hydrocarbons, acetaldehyde, acetone, butanone, acetic acid, or a mixture thereof.

23. The process of claim 21, wherein the fluidizing medium comprises one or more byproducts formed in step (b).

24. The process of claim 23, wherein process further comprises the steps of:
(g) separating the byproducts from the light olefins; and
(h) directing the byproducts to the one or more of the plurality of conduits.

25. The process of claim 21, wherein the one or more of the plurality of conduits comprise a conduit in fluid communication between the disengaging zone and one or more of the stripping unit or the fluidized reactor.

26. The process of claim 21, wherein the one or more of the plurality of conduits comprise a conduit in fluid communication between the catalyst regenerator and one or more of the disengaging zone, the catalyst cooler, the standpipe entry zone, the standpipe or the fluidized reactor.

27. The process of claim 21, wherein the one or more of the plurality of conduits comprise a conduit in fluid communication between the catalyst cooler and one or more of the disengaging zone, the standpipe, the standpipe entry zone, or the fluidized reactor.

28. The process of claim 21, wherein a superficial gas velocity of from about 0.1 to about 1.0 meters/second is formed in the one or more of the plurality of conduits.

29. The process of claim 28, wherein the superficial gas velocity is from about 0.2 to about 0.8 meters/second.

30. The process of claim 21, wherein the second conditions are effective to convert at least a portion of the fluidizing medium to additional light olefins.

31. The process of claim 30, wherein the second conditions comprise a temperature of from about 350° C. to about 1000° C. and a superficial gas velocity in an upward direction of from about 0.1 to about 1.0 m/s.

32. The process of claim 31, wherein the second conditions comprise a temperature of from about 400° C. to about 800° C. and a superficial gas velocity in an upward direction of from about 0.2 to about 0.8 m/s.

33. The process of claim 30, wherein the second conditions comprise a WHSV of less than 5 $hr^{-1}$.

34. The process of claim 33, wherein the WHSV is less than 3 $hr^{-1}$.

35. The process of claim 30, wherein the conversion of the at least a portion of the fluidizing medium to additional light olefins occurs at a weight percent conversion of at least 10 percent.

36. The process of claim 35, wherein the conversion of the at least a portion of the fluidizing medium to additional light olefins occurs at a weight percent conversion of at least 30 percent.

37. The process of claim 21, wherein the first conditions comprise a temperature of from about 204° C. to about 371° C. and a superficial gas velocity of from about 0.11 to about 15 m/s.

38. The process of claim 21, wherein the process further comprises the steps of:
(g) directing a first portion of the molecular sieve catalyst composition to the catalyst regenerator;
(h) heating the first portion in the presence of oxygen under third conditions effective to at least partially regenerate the first portion and form regenerated catalyst; and
(i) directing the regenerated catalyst to one or more of the standpipe, the disengaging zone, the standpipe entry zone or to the one or more of the plurality of conduits.

39. The process of claim 37, wherein the process further comprises the step of:
(j) contacting the regenerated catalyst with the fluidizing medium under conditions effective to increase the selectivity of the regenerated catalyst for light olefins.

40. The process of claim 21, wherein the fluidizing medium further comprises steam.

41. The process of claim 21, wherein the molecular sieve catalyst composition comprises a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, intergrown forms thereof, and mixtures thereof.

42. A process for forming light olefins, the process comprising the steps of:
(a) contacting an oxygenate with a first molecular sieve catalyst composition in a fluidized reactor under first conditions effective to convert the oxygenate to light olefins;
(b) directing the first molecular sieve catalyst composition and the light olefins to a disengaging zone;
(c) yielding the light olefins from the disengaging zone;
(d) directing the first molecular sieve catalyst composition from the disengaging zone to a standpipe;
(e) adding a second molecular sieve catalyst composition to one or more of the standpipe, the disengaging zone or an optional standpipe entry zone;
(f) contacting the second molecular sieve catalyst composition with a fluidizing medium selected from one or more of methanol, dimethyl ether, C4+ olefins, C4+ hydrocarbons, acetaldehyde, acetone, butanone, acetic acid and mixtures thereof under second conditions effective to increase the selectivity of the second molecular sieve catalyst composition for light olefins; and (g) directing the first and second molecular sieve catalyst compositions in a fluidized manner from the standpipe back to the fluidized reactor.

43. The process of claim 42, wherein the second molecular sieve catalyst composition comprises regenerated catalyst.

44. The process of claim 42, wherein the second molecular sieve catalyst composition comprises fresh catalyst.

45. The process of claim 42, wherein the fluidizing medium is selected from one or more byproducts formed in step (a).

46. The process of claim 45, wherein the process further comprises the steps of:
   (h) separating the byproducts from the light olefins; and
   (i) directing the byproducts to one or more of the standpipe, the disengaging zone, or the optional standpipe entry zone.

47. The process of claim 42, wherein the fluidizing medium creates a superficial gas velocity in an upward direction within the standpipe.

48. The process of claim 47, wherein the first and second molecular sieve catalyst compositions are transported in a downward direction while in the standpipe.

49. The process of claim 47, wherein the superficial gas velocity is from about 0.1 to about 1.0 meters/second.

50. The process of claim 49, wherein the superficial gas velocity is from about 0.2 to about 0.8 meters/second.

51. The process of claim 42, wherein the fluidizing medium contacts the first molecular sieve catalyst composition in one or both of steps (f) and (g) under third conditions effective to convert at least a portion of the fluidizing medium to additional light olefins.

52. The process of claim 51, wherein the third conditions comprise a temperature of from about 350° C. to about 1000° C. and a superficial gas velocity in an upward direction of from about 0.1 to about 1.0 m/s.

53. The process of claim 52, wherein the third conditions comprise a temperature of from about 400° C. to about 800° C. and a superficial gas velocity in an upward direction of from about 0.2 to about 0.8 m/s.

54. The process of claim 51, wherein the conversion of the at least a portion of the fluidizing medium to additional light olefins occurs at a WHSV of less than 5 hr$^{-1}$.

55. The process of claim 54, wherein the WHSV is less than 3 hr$^{-1}$.

56. The process of claim 51, wherein the conversion of the at least a portion of the fluidizing medium to additional light olefins occurs at a weight percent conversion of at least 10 percent.

57. The process of claim 56, wherein the conversion of the at least a portion of the fluidizing medium to additional light olefins occurs at a weight percent conversion of at least 30 percent.

58. The process of claim 42, wherein the fluidizing medium contacts the second molecular sieve catalyst composition in one or both of steps (f) and (g) under third conditions effective to convert at least a portion of the fluidizing medium to additional light olefins.

59. The process of claim 58, wherein the third conditions comprise a temperature of from about 350° C. to about 1000° C. and a superficial gas velocity in an upward direction of from about 0.1 to about 1.0 m/s.

60. The process of claim 59, wherein the third conditions comprise a temperature of from about 400° C. to about 800° C. and a superficial gas velocity in an upward direction of from about 0.2 to about 1.0 m/s.

61. The process of claim 42, wherein the first conditions comprise a temperature of from about 204° C. to about 371° C. and a superficial gas velocity of from about 0.11 to about 15 m/s.

62. The process of claim 42, wherein the fluidizing medium further comprises steam.

63. The process of claim 42, wherein the first molecular sieve catalyst composition comprises a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, intergrown forms thereof, and mixtures thereof.

64. The process of claim 42, wherein the second molecular sieve catalyst composition comprises a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, intergrown forms thereof, and mixtures thereof.

65. The process of claim 42, wherein the first molecular sieve catalyst composition is at least partially deactivated in step (a) to form a coked catalyst, the process further comprising the step of:
   (h) directing the coked catalyst from the disengaging zone to a catalyst regenerator; and
   (i) heating the coked catalyst in the presence of oxygen under third conditions effective to at least partially regenerate the coked catalyst and form the second molecular sieve catalyst composition.

66. A process for producing light olefins, the process comprising the steps of:
   (a) contacting an oxygenate with a molecular sieve catalyst composition in a fluidized reactor under first conditions effective to convert the oxygenate to the light olefins;
   (b) directing the molecular sieve catalyst composition and the light olefins to a disengaging zone;
   (c) yielding the light olefins from the disengaging zone;
   (d) directing the molecular sieve catalyst composition from the disengaging zone to a standpipe entry zone;
   (e) fluidizing the molecular sieve catalyst composition in the standpipe entry zone with a fluidizing medium, wherein the fluidizing medium is selected from one or more of methanol, dimethyl ether, C4+ olefins, C4+ hydrocarbons, acetaldehyde, acetone, butanone, acetic acid, byproducts formed in step (a) or a mixture thereof;
   (f) directing the molecular sieve catalyst composition from the standpipe entry zone to a standpipe; and
   (g) transporting the molecular sieve catalyst composition from the standpipe to the fluidized reactor.

67. The process of claim 66, wherein the fluidizing medium is selected from one or more of methanol, dimethyl ether, C4+ olefins, C4+ hydrocarbons, acetaldehyde, acetone, butanone, acetic acid, or a mixtures thereof.

68. The process of claim 66, wherein the fluidizing medium comprises one or more byproducts formed in step (a).

69. The process of claim 68, wherein the process further comprises the steps of:
   (h) separating the byproducts from the light olefins; and
   (i) directing the byproducts to the standpipe entry zone.

70. The process of claim 66, wherein the fluidizing medium contacts the molecular sieve catalyst composition in one or more of steps (e), (f) or (g) under second conditions effective to convert at least a portion of the fluidizing medium to additional light olefins.

71. The process of claim 70, wherein the second conditions comprise a temperature of from about 350° C. to about 1000° C. and a superficial gas velocity in an upward direction of from about 0.1 to about 1.0 m/s.

72. The process of claim 71, wherein the second conditions comprise a temperature of from about 400° C. to about 800° C. and a superficial gas velocity in an upward direction of from about 0.2 to about 0.8 m/s.

73. The process of claim 70, wherein the second conditions comprise a WHSV of less than 5 $hr^{-1}$.

74. The process of claim 73, wherein the WHSV is less than 3 $hr^{-1}$.

75. The process of claim 70, wherein the conversion of the at least a portion of the fluidizing medium to additional light olefins occurs at a weight percent conversion of at least 10 percent.

76. The process of claim 75, wherein the conversion of the at least a portion of the fluidizing medium to additional light olefins occurs at a weight percent conversion of at least 30 percent.

77. The process of claim 66, wherein the first conditions comprise a temperature of from about 204° C. to about 371° C. and a superficial gas velocity of from about 0.11 to about 15 m/s.

78. The process of claim 66, wherein the process further comprises the steps of:

(h) directing a first portion of the molecular sieve catalyst composition to a catalyst regenerator;

(i) heating the first portion in the presence of oxygen under third conditions effective to at least partially regenerate the first portion and form regenerated catalyst; and (j) directing the regenerated catalyst to one or more of the disengaging zone, the standpipe entry zone or the standpipe.

79. The process of claim 78, wherein the process further comprises the step of:

(k) contacting the regenerated catalyst with the fluidizing medium under conditions effective to increase the selectivity of the regenerated catalyst for light olefins.

80. The process of claim 66, wherein the fluidizing medium further comprises steam.

81. The process of claim 66, wherein the molecular sieve catalyst composition comprises a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, intergrown forms thereof, and mixtures thereof.

* * * * *